US009833184B2

(12) United States Patent
Derchak et al.

(10) Patent No.: US 9,833,184 B2
(45) Date of Patent: Dec. 5, 2017

(54) IDENTIFICATION OF EMOTIONAL STATES USING PHYSIOLOGICAL RESPONSES

(75) Inventors: P. Alexander Derchak, Summit, NJ (US); Lance Jonathan Myers, Ventura, CA (US)

(73) Assignee: adidas AG, Herzogenaurach (DE)

( * ) Notice: Subject to any disclaimer, the term of this patent is extended or adjusted under 35 U.S.C. 154(b) by 1259 days.

(21) Appl. No.: 11/925,109

(22) Filed: Oct. 26, 2007

(65) Prior Publication Data

US 2008/0221401 A1 Sep. 11, 2008

Related U.S. Application Data (60) Provisional application No. 60/863,216, filed on Oct. 27, 2006.

(51) Int. Cl.
*A61B 5/00* (2006.01)
*A61B 5/16* (2006.01)
*G06F 19/00* (2011.01)

(52) U.S. Cl.
CPC .............. *A61B 5/16* (2013.01); *A61B 5/6805* (2013.01); *G06F 19/345* (2013.01); *A61B 5/7267* (2013.01); *G06F 19/3406* (2013.01); *G06F 2203/011* (2013.01)

(58) Field of Classification Search
USPC ................... 600/31, 544, 485, 483, 300–301
See application file for complete search history.

(56) References Cited

U.S. PATENT DOCUMENTS

| | | | |
|---|---|---|---|
| 3,534,727 A | 10/1970 | Roman | |
| 3,731,184 A | 5/1973 | Goldberg et al. | |
| 3,874,368 A | 4/1975 | Asrican | |
| 3,926,177 A | 12/1975 | Hardway, Jr. et al. | |
| 4,016,868 A | 4/1977 | Allison | 128/2.1 E |
| 4,033,332 A | 7/1977 | Hardway, Jr. et al. | |
| 4,102,331 A | 7/1978 | Grayzel et al. | |
| 4,258,718 A | 3/1981 | Goldman | |
| 4,267,845 A | 5/1981 | Robertson, Jr. et al. | |
| 4,289,142 A | 9/1981 | Kearns | |
| 4,306,567 A | 12/1981 | Krasner | 128/671 |

(Continued)

FOREIGN PATENT DOCUMENTS

| | | |
|---|---|---|
| DE | 4214263 | 11/1993 |
| EP | 0262778 | 4/1988 |

(Continued)

OTHER PUBLICATIONS

6th Portuguese Conference on Biomedical Engineering, "BioEng' 2001 Conference Papers", (Jun. 2001) 6 pages.

(Continued)

*Primary Examiner* — Shirley Jian
(74) *Attorney, Agent, or Firm* — Sterne, Kessler, Goldstein & Fox P.L.L.C.

(57) ABSTRACT

The invention provides a method for automatically identifying emotional states of a person in real-time based on physiological responses by exposing a person to a stimulus, measuring the person's physiological response to the stimulus, and comparing the measured physiological response to a known baseline physiological. The deviation of the measured physiological response from the baseline physiological response is determinative of the emotional state.

18 Claims, 5 Drawing Sheets

(56) References Cited

U.S. PATENT DOCUMENTS

| | | | |
|---|---|---|---|
| 4,308,872 A | 1/1982 | Watson et al. ............... 128/725 |
| 4,373,534 A | 2/1983 | Watson ......................... 128/725 |
| 4,387,722 A | 6/1983 | Kearns |
| 4,433,693 A | 2/1984 | Hochstein ..................... 128/721 |
| 4,446,872 A | 5/1984 | Marsoner et al. |
| 4,452,252 A | 6/1984 | Sackner ........................ 128/671 |
| 4,456,015 A | 6/1984 | Sackner ........................ 128/721 |
| 4,463,764 A | 8/1984 | Anderson et al. ............ 128/719 |
| 4,494,553 A | 1/1985 | Sciarra et al. |
| 4,537,196 A | 8/1985 | Phillipps et al. |
| 4,545,376 A | 10/1985 | Beiter |
| 4,546,777 A | 10/1985 | Groch et al. |
| 4,548,204 A | 10/1985 | Groch et al. |
| 4,549,552 A | 10/1985 | Groch et al. |
| 4,572,197 A | 2/1986 | Moore et al. |
| 4,580,572 A | 4/1986 | Granek et al. |
| 4,648,407 A | 3/1987 | Sackner ........................ 128/721 |
| 4,672,975 A | 6/1987 | Sirota |
| 4,753,988 A | 6/1988 | Henton et al. ................. 525/73 |
| 4,777,962 A | 10/1988 | Watson et al. ............... 128/716 |
| 4,796,639 A | 1/1989 | Snow et al. .................. 128/719 |
| 4,800,495 A | 1/1989 | Smith ...................... 364/413.03 |
| 4,807,640 A | 2/1989 | Watson et al. ............... 128/721 |
| 4,815,473 A | 3/1989 | Watson et al. ............... 128/721 |
| 4,817,625 A | 4/1989 | Miles ............................ 128/721 |
| 4,819,752 A | 4/1989 | Zelin |
| 4,834,109 A | 5/1989 | Watson ......................... 128/721 |
| 4,860,766 A | 8/1989 | Sackner ........................ 128/748 |
| 4,863,265 A | 9/1989 | Flower et al. |
| 4,867,571 A | 9/1989 | Frick et al. |
| 4,889,131 A | 12/1989 | Salem et al. |
| 4,909,260 A | 3/1990 | Salem et al. |
| 4,911,167 A | 3/1990 | Corenman et al. |
| 4,920,969 A | 5/1990 | Suzuki et al. |
| 4,928,692 A | 5/1990 | Goodman et al. |
| 4,934,372 A | 6/1990 | Corenman et al. |
| 4,955,379 A | 9/1990 | Hall |
| 4,960,118 A | 10/1990 | Pennock .................... 128/200.4 |
| 4,966,155 A | 10/1990 | Jackson ........................ 128/671 |
| 4,972,842 A | 11/1990 | Korten et al. ................ 128/716 |
| 4,981,139 A | 1/1991 | Pfohl |
| 4,986,277 A | 1/1991 | Sackner ........................ 128/672 |
| 5,007,427 A | 4/1991 | Suzuki et al. ................ 128/659 |
| 5,025,791 A | 6/1991 | Niwa |
| 5,036,857 A | 8/1991 | Semmlow et al. |
| 5,040,540 A | 8/1991 | Sackner ........................ 128/672 |
| 5,074,129 A | 12/1991 | Matthew .......................... 66/192 |
| 5,076,801 A | 12/1991 | Schroll |
| 5,099,841 A | 3/1992 | Heinonen et al. |
| 5,099,855 A | 3/1992 | Yount |
| 5,111,817 A | 5/1992 | Clark et al. |
| 5,131,399 A | 7/1992 | Sciarra .......................... 128/671 |
| 5,143,089 A | 9/1992 | Alt |
| 5,159,935 A | 11/1992 | Sackner et al. .............. 128/721 |
| 5,173,151 A | 12/1992 | Namose |
| 5,178,151 A | 1/1993 | Sackner ........................ 128/672 |
| 5,224,479 A | 7/1993 | Sekine |
| 5,241,300 A | 8/1993 | Buschmann |
| 5,271,551 A | 12/1993 | Roepke |
| 5,295,490 A | 3/1994 | Dodakian |
| 5,299,120 A | 3/1994 | Kaestle |
| 5,301,678 A | 4/1994 | Watson et al. ............... 128/721 |
| 5,329,932 A | 7/1994 | Yount |
| 5,331,968 A | 7/1994 | Williams et al. ............. 128/721 |
| 5,333,106 A | 7/1994 | Lanpher et al. |
| 5,348,008 A | 9/1994 | Bornn et al. ................. 128/642 |
| 5,353,793 A | 10/1994 | Bornn et al. ................. 128/642 |
| 5,416,961 A | 5/1995 | Vinay ........................... 128/165 |
| 5,447,164 A | 9/1995 | Shaya et al. ................. 128/710 |
| 5,447,166 A * | 9/1995 | Gevins ................. A61B 5/0484<br>128/925 |
| RE35,122 E | 12/1995 | Coreman et al. ............. 600/633 |
| 5,520,192 A | 5/1996 | Kitney et al. |
| 5,533,511 A | 7/1996 | Kaspari et al. ............... 128/672 |
| 5,535,738 A | 7/1996 | Estes et al. |
| 5,544,661 A | 8/1996 | Davis et al. .................. 128/700 |
| 5,564,429 A | 10/1996 | Bornn et al. ................. 128/696 |
| 5,577,510 A | 11/1996 | Chittum et al. .............. 128/709 |
| 5,582,337 A | 12/1996 | McPherson et al. |
| 5,584,295 A | 12/1996 | Muller et al. |
| 5,588,425 A | 12/1996 | Sackner et al. .............. 128/632 |
| 5,601,088 A | 2/1997 | Swanson et al. ............. 128/697 |
| 5,611,085 A | 3/1997 | Rasmussen |
| 5,617,847 A | 4/1997 | Howe |
| 5,619,291 A * | 4/1997 | Putnam ..................... A61B 5/16<br>351/239 |
| 5,676,138 A * | 10/1997 | Zawilinski ..................... 600/301 |
| 5,694,939 A | 12/1997 | Cowings ....................... 128/671 |
| 5,718,234 A | 2/1998 | Warden et al. |
| 5,719,950 A | 2/1998 | Osten et al. .................. 382/115 |
| 5,720,709 A | 2/1998 | Schnall |
| 5,724,025 A | 3/1998 | Tavori |
| 5,749,365 A | 5/1998 | Magill ........................... 128/671 |
| 5,820,567 A | 10/1998 | Mackie .......................... 600/519 |
| 5,825,293 A | 10/1998 | Ahmed |
| 5,848,027 A | 12/1998 | Dotter ............................. 368/10 |
| 5,882,307 A | 3/1999 | Wright et al. |
| 5,899,855 A | 5/1999 | Brown ........................... 600/301 |
| 5,913,830 A | 6/1999 | Miles ............................. 600/535 |
| 5,921,920 A | 7/1999 | Marshall et al. |
| 5,937,854 A | 8/1999 | Stenzler |
| 5,952,993 A * | 9/1999 | Matsuda ................. G06T 13/20<br>345/421 |
| 5,983,129 A * | 11/1999 | Cowan ............... A61B 5/04842<br>128/905 |
| 5,989,193 A | 11/1999 | Sullivan |
| 5,991,922 A | 11/1999 | Banks ................................ 2/69 |
| 6,001,065 A * | 12/1999 | DeVito ........................... 600/544 |
| 6,002,952 A | 12/1999 | Diab et al. |
| 6,015,388 A | 1/2000 | Sackner et al. .............. 600/529 |
| 6,018,677 A | 1/2000 | Vidrine et al. |
| 6,035,154 A | 3/2000 | Takahata et al. |
| 6,047,203 A | 4/2000 | Sackner et al. .............. 600/388 |
| 6,066,093 A | 5/2000 | Kelly et al. ................... 600/386 |
| 6,067,462 A | 5/2000 | Diab et al. .................... 600/310 |
| 6,068,568 A | 5/2000 | Kozakura et al. ............ 474/212 |
| 6,070,098 A | 5/2000 | Moore-Ede et al. ......... 600/544 |
| 6,120,441 A | 9/2000 | Griebel |
| 6,142,953 A | 11/2000 | Burton et al. ................. 600/534 |
| 6,145,551 A | 11/2000 | Jayaraman et al. |
| 6,171,258 B1 * | 1/2001 | Karakasoglu et al. ....... 600/529 |
| 6,179,786 B1 | 1/2001 | Young |
| 6,190,314 B1 * | 2/2001 | Ark et al. ...................... 600/300 |
| 6,198,394 B1 | 3/2001 | Jacobsen et al. |
| 6,223,072 B1 | 4/2001 | Mika et al. .................... 600/510 |
| 6,254,536 B1 * | 7/2001 | DeVito ........................... 600/300 |
| 6,254,552 B1 | 7/2001 | Lewis et al. ................... 600/603 |
| 6,261,238 B1 | 7/2001 | Gavriely ....................... 600/532 |
| 6,273,859 B1 | 8/2001 | Remmers et al. |
| 6,287,264 B1 | 9/2001 | Hoffman |
| 6,302,844 B1 | 10/2001 | Walker et al. ................. 600/300 |
| 6,306,088 B1 | 10/2001 | Krausman et al. |
| 6,341,504 B1 | 1/2002 | Istook ........................ 66/172 E |
| 6,361,501 B1 | 3/2002 | Amano et al. |
| 6,381,482 B1 | 4/2002 | Jayaraman et al. |
| 6,413,225 B1 | 7/2002 | Sackner et al. .............. 600/529 |
| 6,419,636 B1 | 7/2002 | Young et al. |
| 6,436,057 B1 | 8/2002 | Goldsmith et al. ........... 600/586 |
| 6,443,890 B1 | 9/2002 | Schulze et al. |
| 6,449,504 B1 | 9/2002 | Conley et al. ................ 600/523 |
| 6,454,719 B1 | 9/2002 | Greenhut |
| 6,461,307 B1 | 10/2002 | Kristbjarnarson et al. |
| 6,463,385 B1 | 10/2002 | Fry |
| 6,478,736 B1 | 11/2002 | Mault |
| 6,483,929 B1 | 11/2002 | Murakami et al. ........... 382/115 |
| 6,485,431 B1 | 11/2002 | Campbell |
| 6,506,153 B1 | 1/2003 | Littek et al. |
| 6,511,424 B1 | 1/2003 | Moore-Ede et al. ......... 600/300 |
| 6,513,532 B2 | 2/2003 | Mault et al. |
| 6,551,252 B2 | 4/2003 | Sackner et al. .............. 600/536 |
| 6,579,231 B1 | 6/2003 | Phipps .......................... 600/300 |
| 6,604,115 B1 | 8/2003 | Gary, Jr. et al. ........... 707/104.1 |
| 6,633,772 B2 | 10/2003 | Ford et al. .................... 600/345 |
| 6,647,252 B2 | 11/2003 | Smith et al. |

(56) References Cited

U.S. PATENT DOCUMENTS

| | | | |
|---|---|---|---|
| 6,656,127 B1 | 12/2003 | Ben-Oren et al. | 600/532 |
| 6,687,523 B1 | 2/2004 | Jayaramen et al. | |
| 6,699,194 B1 | 3/2004 | Diab et al. | |
| 6,702,752 B2 | 3/2004 | Dekker | |
| 6,709,402 B2 | 3/2004 | Dekker | |
| 6,721,594 B2 | 4/2004 | Conley et al. | 600/523 |
| 6,723,055 B2 | 4/2004 | Hoffman | 600/538 |
| 6,726,636 B2 | 4/2004 | Der Ghazarian et al. | |
| 6,727,197 B1 | 4/2004 | Wilson et al. | 442/301 |
| 6,747,561 B1 | 6/2004 | Reeves | |
| 6,775,389 B2 | 8/2004 | Harrison et al. | |
| 6,783,498 B2 | 8/2004 | Sackner et al. | 600/481 |
| 6,801,916 B2 | 10/2004 | Roberge et al. | 707/101 |
| 6,817,979 B2 | 11/2004 | Nihtila | |
| 6,858,006 B2 | 2/2005 | MacCarter et al. | |
| 6,881,192 B1 | 4/2005 | Park | 600/529 |
| 6,941,775 B2 | 9/2005 | Sharma | |
| 6,942,615 B2* | 9/2005 | Suzuki et al. | 600/300 |
| 6,960,168 B2* | 11/2005 | Yanagidaira et al. | 600/300 |
| 6,961,448 B2 | 11/2005 | Nichols et al. | 382/115 |
| 6,970,731 B1 | 11/2005 | Jayaramen et al. | |
| 6,993,378 B2 | 1/2006 | Wiederhold et al. | |
| 7,001,337 B2 | 2/2006 | Dekker | |
| 7,073,129 B1 | 7/2006 | Robarts et al. | |
| 7,077,810 B2 | 7/2006 | Lange et al. | |
| 7,081,095 B2 | 7/2006 | Lynn et al. | 600/538 |
| 7,082,327 B2 | 7/2006 | Houben | |
| 7,099,714 B2 | 8/2006 | Houben | 600/509 |
| 7,104,962 B2 | 9/2006 | Lomask et al. | 600/529 |
| 7,154,398 B2 | 12/2006 | Chen et al. | |
| 7,207,948 B2 | 4/2007 | Coyle | |
| 7,254,516 B2 | 8/2007 | Case, Jr. et al. | |
| 7,267,652 B2 | 9/2007 | Coyle et al. | |
| 7,319,385 B2 | 1/2008 | Ruha | |
| 7,547,279 B2* | 6/2009 | Kim et al. | 600/300 |
| 7,559,902 B2 | 7/2009 | Ting et al. | |
| 7,604,603 B2 | 10/2009 | Sackner et al. | |
| 7,670,295 B2 | 3/2010 | Sackner et al. | |
| 7,727,161 B2 | 6/2010 | Coyle et al. | |
| 7,762,953 B2 | 7/2010 | Derchak et al. | |
| 7,809,433 B2 | 10/2010 | Keenan | |
| 7,878,979 B2 | 2/2011 | Derchak | |
| 8,684,742 B2* | 4/2014 | Siefert | G09B 5/10 434/236 |
| 9,579,457 B2* | 2/2017 | Osorio | A61M 5/1723 |
| 2001/0049471 A1* | 12/2001 | Suzuki et al. | 600/300 |
| 2002/0032386 A1 | 3/2002 | Sackner et al. | |
| 2002/0084130 A1 | 7/2002 | Der Ghazarian | |
| 2002/0090667 A1 | 7/2002 | Ratcliffe et al. | |
| 2002/0123701 A1 | 9/2002 | Eriksen | |
| 2003/0013981 A1* | 1/2003 | Gevins et al. | 600/544 |
| 2003/0100843 A1 | 5/2003 | Hoffman | |
| 2003/0135097 A1 | 7/2003 | Wiederhold et al. | |
| 2003/0135127 A1 | 7/2003 | Sackner et al. | 600/536 |
| 2003/0139654 A1* | 7/2003 | Kim et al. | 600/300 |
| 2003/0166996 A1* | 9/2003 | Kim et al. | 600/300 |
| 2003/0185408 A1 | 10/2003 | Causevic | 381/94.1 |
| 2003/0187341 A1 | 10/2003 | Sackner et al. | |
| 2003/0195398 A1* | 10/2003 | Suzuki et al. | 600/300 |
| 2003/0236451 A1* | 12/2003 | El-Nokaly et al. | 600/300 |
| 2004/0010420 A1 | 1/2004 | Rooks | |
| 2004/0019289 A1 | 1/2004 | Ross | |
| 2004/0030224 A1 | 2/2004 | Sotos et al. | |
| 2004/0111040 A1 | 6/2004 | Ni et al. | 600/534 |
| 2004/0117204 A1 | 6/2004 | Mazar | |
| 2004/0122334 A1 | 6/2004 | Yamashiro | |
| 2004/0143194 A1 | 7/2004 | Kihara et al. | 600/534 |
| 2004/0204636 A1 | 10/2004 | Diab et al. | 600/323 |
| 2004/0210147 A1 | 10/2004 | Houben | 600/509 |
| 2004/0225227 A1 | 11/2004 | Newman | |
| 2004/0249299 A1 | 12/2004 | Cobb | 600/529 |
| 2005/0027207 A1 | 2/2005 | Westbrook et al. | |
| 2005/0054941 A1 | 3/2005 | Ting et al. | 600/529 |
| 2005/0076908 A1 | 4/2005 | Lee et al. | 128/204.23 |
| 2005/0102246 A1* | 5/2005 | Movellan et al. | 706/12 |
| 2005/0119586 A1 | 6/2005 | Coyle et al. | 600/538 |
| 2005/0125970 A1 | 6/2005 | Nolan | |
| 2005/0211247 A1 | 9/2005 | Noda et al. | |
| 2005/0228234 A1 | 10/2005 | Yang | 600/300 |
| 2005/0240087 A1 | 10/2005 | Keenan et al. | 600/301 |
| 2005/0256385 A1 | 11/2005 | Diab et al. | |
| 2005/0272984 A1* | 12/2005 | Huiku | 600/301 |
| 2006/0000420 A1 | 1/2006 | Martin Davies | |
| 2006/0009702 A1* | 1/2006 | Iwaki et al. | 600/520 |
| 2006/0015034 A1* | 1/2006 | Martinerie et al. | 600/544 |
| 2006/0036183 A1 | 2/2006 | Sackner et al. | 600/481 |
| 2006/0047187 A1* | 3/2006 | Goyal et al. | 600/300 |
| 2006/0074334 A1 | 4/2006 | Coyle | |
| 2006/0122528 A1 | 6/2006 | Gal | |
| 2006/0178591 A1 | 8/2006 | Hempfling | 600/529 |
| 2006/0258914 A1 | 11/2006 | Derchak et al. | |
| 2006/0293609 A1 | 12/2006 | Stahmann et al. | |
| 2007/0027368 A1 | 2/2007 | Collins et al. | |
| 2007/0050715 A1 | 3/2007 | Behar | |
| 2007/0100622 A1 | 5/2007 | Tavares | |
| 2007/0150006 A1 | 6/2007 | Libbus et al. | |
| 2007/0177770 A1 | 8/2007 | Derchak et al. | |
| 2007/0208262 A1 | 9/2007 | Kovacs | |
| 2007/0209669 A1 | 9/2007 | Derchak | |
| 2007/0270671 A1 | 11/2007 | Gal | |
| 2008/0015454 A1 | 1/2008 | Gal | |
| 2008/0027341 A1 | 1/2008 | Sackner et al. | |
| 2008/0045815 A1 | 2/2008 | Derchak et al. | |
| 2008/0051839 A1 | 2/2008 | Libbus et al. | |
| 2008/0065468 A1* | 3/2008 | Berg et al. | 705/10 |
| 2008/0082018 A1 | 4/2008 | Sackner et al. | |
| 2008/0201144 A1* | 8/2008 | Song et al. | 704/236 |
| 2008/0214903 A1* | 9/2008 | Orbach | 600/301 |
| 2008/0221401 A1 | 9/2008 | Derchak et al. | |
| 2008/0269644 A1 | 10/2008 | Ray | |
| 2009/0131759 A1 | 5/2009 | Sims et al. | |
| 2010/0039618 A1* | 2/2010 | De Lemos | A61B 3/113 351/209 |
| 2010/0274100 A1 | 10/2010 | Behar et al. | |
| 2011/0009766 A1 | 1/2011 | McCool | |
| 2017/0080856 A1* | 3/2017 | Enomoto | B60Q 9/00 |

FOREIGN PATENT DOCUMENTS

| | | |
|---|---|---|
| EP | 0875199 A | 11/1998 |
| GB | 1596298 A | 8/1981 |
| GB | 2116725 | 9/1983 |
| JP | 53126786 A | 6/1978 |
| JP | 58109031 A | 6/1983 |
| JP | 6337933 A | 2/1988 |
| JP | 1091834 | 4/1989 |
| JP | 5168602 | 7/1993 |
| JP | 5298589 | 11/1993 |
| JP | 7227383 A | 8/1995 |
| JP | 2001516253 A | 9/1998 |
| JP | 2001104259 A | 4/2001 |
| WO | WO9810699 | 3/1998 |
| WO | WO0128420 | 4/2001 |
| WO | WO0176467 | 10/2001 |
| WO | WO02060370 | 8/2002 |
| WO | WO02069878 | 12/2002 |
| WO | WO03022149 | 3/2003 |
| WO | WO2004/019503 | 3/2005 |
| WO | WO2005/115242 | 12/2005 |
| WO | WO2006002338 | 1/2006 |
| WO | WO2006009830 | 1/2006 |
| WO | WO 2006/090371 A2 | 8/2006 |
| WO | WO2007021645 | 2/2007 |
| WO | WO2007069111 | 6/2007 |
| WO | WO 2007/089751 | 8/2007 |
| WO | WO2009074973 | 6/2009 |
| WO | WO2010027515 | 3/2010 |

OTHER PUBLICATIONS

Aliverti. et al., "Chronic Obstructive Pulmonary Disease: Regional Chest Wall Volumes During Exercise in Chronic Obstructive Pulmonary Disease." *Thorax*, 59:210-216, 7 pages, 2004.

(56) References Cited

OTHER PUBLICATIONS

Almeida et al., "Wavelet Transform Based Matlab System for the Detection and Delineation of QRS Complexes in Ambulatory ECG Recordingd", *6th Portuguese Conference on Biomedical Engineering* (Jun. 2001), 2 pages.

Anderer et al., "Artifact Processing in Computerized Analysis of Sleep EEG—A Review" *Neuropsychobiology*, 40:150-157 (1999), 8 pages.

Bianchi et al., "Extraction of the Respiration Influence From the Heart Rate Variability Signal by Means of Lattice Adaptive Filter", *IEEE Transactions on Biomedical Engineering*, pp. 121-122 (1994), 2 pages.

National Biometric Test Center, "The Functions of Biometric Indentification Devices", *San Jose State University Biometrics Publications*, www.engr.sjsu.edu/biometrics/publications_tech. html (printed Jul. 28, 2005), 25 pages.

National Biometric Test Center, "Biometric Technology—Testing, Evaluation, Results", *San Jose State University Biometrics Publications*, www.engr.sjsu.edu/biometrics/publications_tech.html (printed Jul. 28, 2005), 13 pages.

Blechert et al., "Identifying Anxiety States Using Broad Sampling and Advance Processing of Peripheral Physiological Information," *Psychosom Med Dec. 2007*;69(9):935-43 Epub Nov. 8, 2007 6 pages.

Bloch et al., "Specific respiratory patterns distinguish among human basic emotions," *International Journal of Psychophysiology*, 11:141-154 (1991), 14 pages.

Bonnet et al., "EEG Arousals: Scoring Rules and Examples, A Preliminary Report from the Sleep Disorders Atlas Task Force of the American Sleep Disorders Association," *Sleep*, 152(2): 173-184 (1992), 12 pages.

Brack, "Cheyne-Stokes respiration in patients with congestive heart failure," Swiss Med Weekly 133:605-610 (2003), 7 pages.

Costa et al., "Multiscale Entropy Analysis of Complex Physiologic Time Series," Physical Review Letters 89(6):068102-1-4 Aug. 5, 2002, 4 pages.

Coyle et al., "Home Measurement of Cough Indicates Circadian Frequency Pattern and Abnormal Distribution During Sleep," LifeShirt System, study sponsored by Pfizer, Inc., Jun. 2004, 1 page.

Fahrenberg, "Origins and Developments of Ambulatory Monitoring and Assessment," (2001), 30 pages.

Gore Electronic Products, "Expanded PTFE Insulation Material", www.goreelectronics.com (visited Aug. 2005), 4 pages.

Grossman et al., "Reliability of Respiratory Tidal Volume Estimation by Means of Ambulatory Inductive Plethysmography," Biomed Sci Instrum 42:192-8 (2006), 6 pages.

Grossman et al., "A Comparison of Tnree Quantification Methods for Estimation of Respiratory Sinus Arrhythmia", Psychophycology, 27(6):702-714 (1990), 17 pages.

Istepanian et al., "Microcontroller-Based Underwater Acoustic ECG Telemetry System", IEEE Transactions on Information Technology in Biomedicine, 1(2):150-154 (Jun. 1997), 5 pages.

Keenan et al., "Adaptive Filtering of Heart Rate Signals for an Improved Measure of Sympathovagal Balance," Jan. 1, 2005, 8 pages.

Klabunde, "Electrocardiogram (EKG, ECG)", Cardiovascular Physiology Concepts, www.cvphysiology.com (visited Mar. 2005), 3 pages.

Lake et al., "Sample entropy analysis of neonatal heart rate variability," Am J Physiol Regul Integr Comp 283:R789-97 (2002), 10 pages.

Marin et al., "Inspiratory Capacity, Dynamic Hyperinflation, Breathlessness, and Exercise Performance During the 6-Minute-Walk Test in Chronic Obstructive Pulmonary Disease", Am. J. Respir. Crit. Care Med., vol. 163., pp. 1395-1399, (2001), 5 pages.

McCool et al., "Estimates of ventilation from body surface measurements in unstricted subjects," J. Appl. Physiol. 61(3):1114-9 (1986), 6 pages.

McCool et al., "Tidal Volume and Respiratory Timing Derived From a Portable Ventilation Monitor," Chest 122:684-91 (2002), 10 pages.

McNaughton et al., "Metallized Polymer Fibers As Leadwires and Intrafascicular Microelectrodes", J. Neurosci. Methods, 70(1):103-10 (1996), 2 pages.

Micro-Coax, "About Micro-Coax", www.micro-coax.com (visited Aug. 2004), 9 pages.

Niskanen et al., "Software for Advanced HRV Analysis", University of Kuopio Department of Applied Physics Report Series, pp. 1-11 (Feb. 2002), 12 pages.

O'Donnell, "Ventilatory Limitations in Chronic Obstructive Pulmonary Disease", Medicine & Science in Sports & Exercise, pp. S647-S655, (2001), 9 pages.

O'Donnell et al., "Dynamic Hyperinflation and Exercise Intolerance in Chronic Obstructive Pulmonary Disease", Am. J. Respir. Crit. Care Med., 164:770-777 (2001), 8 pages.

Park et al., "Automated Detection and Elimination of Periodic ECG Artifacts in EEG Using the Energy Interval Histogram Method", IEEE Transactions on Biomedical Engineering 49(12):1526-1533 (2002), 8 pages.

Pietraszek et al., "Simple Telemetry System for ECG Recording", Polish J. Med. Phys. & Eng. 2002; 8(3): 193-198, 4 pages.

Rampil, "A Primer for EEG Signal Processing in Anesthesia," Anesthesiology 89(4):980-1002 Oct. 1998, 15 pages.

Richman et al., "Physiological time-series analysis using approximate entropy and sample entropy," Am J. Physiol Circ Physiol 278:H2039-49 (2000), 11 pages.

Signal Consulting Inc., "Inductance of Circular Loop", www.sigcon.com (visited Aug. 2005), 2 pages.

Sijbers et al., "Reduction of ECG and gradient related artifacts in simultaneously recorded human EEG/MRI data," Magnetic Resonance Imaging 18:881-6 (2000), 6 pages.

Snyder et al., "Ventilatory Responses to Hypoxia and High Altitude During Sleep in Aconcagua Climbers," Wilderness and Environmental Medicine 18:138-145 (2007), 8 pages.

Szabo et al., "Prognostic Value of Heart Rate Variability in Chronic Congestive Heart Failure Secondary to Idiopathic or Ischemic Dilated Cardiomypathy," Am J Cardiol. 79:978-980 (1997), 3 pages.

Taylor, et al., "Cigarette smoke inhalation patterns and bronchial reactivity", 1988, Thorax, 43, 65-70.

van Dijk et al., "Determinants of Brachial Artery mean 24 h PulsePressure in Individuals with Type II diabetes mellitus and untreated mild hypertension", Clinical Science (2002), 102, pp. 177-186, 10 pages.

Vogiatzis, et al., "Respiratory Kinematics by Optoelectronic Plethysmography During Exercise in Men and Women.", Eur J of App Physiol, 581-587, 7 pages, 2004, 7 pages.

Wachowski, Andy and Larry, The Matrix, released Mar. 31, 1999 by Warner Bros. Pictures, see 1:26:29, 2:03:10, and 2:04:41, 13 pages.

Wilhelm et al., "Distinguishing Emotional From Physical Activation in Ambulatory Psychophysiological Monitoring," Biomed Sci Instrum 42:458-63 (2006), 6 pages.

Wilhelm et al., "Taking the laboratory to the skies: Ambulatory assesment of self-report, autonomic, and respiratory responses in flyings phobia," Psychophysiology 35:596-606 (1998), 11 pages.

Supplementary Partial European Search Report of the European Patent Office, Application No. EP 06784447.2, dated Jan. 20, 2010, 9 pages.

Supplementary Partial European Search Report of the European Patent Office, Application No. EP 04759405.6, dated Jan. 25, 2011, 4 pages.

International Search Report and the Written Opinion of the International Searching Authority, application No. PCT/US2008/061171, dated Nov. 14, 2008, 10 pages.

International Search Report and the Written Opinion of the International Searching Authority, application No. PCT/US06/60264, dated Jan. 15, 2008, 8 pages.

International Search Report and the Written Opinion of the International Searching Authority, application No. PCT/US2007/82688, dated May 8, 2008, 7 pages.

(56) References Cited

OTHER PUBLICATIONS

International Search Report and the Written Opinion of the International Searching Authority, application No. PCT/US2008/072414, dated Nov. 12, 2008, 7 pages.
Extended European Search Report for Application No. EP 07798146.2, Applicant: adidas AG, mailed Oct. 19, 2010.
Extended European Search Report for Application No. EP 10174873.9, Applicant: adidas AG, mailed Dec. 8, 2010.
Extended European Search Report for Application No. EP 10174680.8, Applicant: adidas AG, mailed Dec. 9, 2010.
Extended European Search Report for Application No. EP 10174876.2, Applicant: adidas AG, mailed Dec. 9, 2010.
Extended European Search Report for Application No. EP 10174881.2, Applicant: adidas AG, mailed Dec. 9, 2010.
Extended European Search Report for Application No. EP 10174683.2, Applicant: adidas AG, mailed Dec. 27, 2010.
Partial European Search Report for Application No. EP 10174885.3, Applicant: adidas AG, mailed Jan. 4, 2011.
Office Action dated Nov. 30, 2010 from Japanese Appl. No. 2006-509897, Adidas AG, Systems and Methods for Respiratory Event Detection, with translation.
Office Action dated Aug. 2, 2010 from U.S. Appl. No. 11/373,822, Sackner, System and Methods for Ambulatory Monitoring of Physiological Signs, filed Mar. 9, 2006.
Office Action dated Sep. 28, 2010 from U.S. Appl. No. 11/503,350, Behar, Systems and Methods for Monitoring Subjects in Potential Physiological Distress, Aug. 10, 2006.
Office Action dated Oct. 15, 2010 from U.S. Appl. No. 11/627,198, Derchak, System and Method for Identity Confirmation Using Physiologic Biometrics to Determine a Physiologic Fingerprint, filed Jan. 25, 2007.
Office Action dated Nov. 18, 2010 from U.S. Appl. No. 11/492,484, Behar, Computer Interfaces Including Physiologically Guided Avatars, filed Jul. 24, 2006.
Office Action dated Jan. 4, 2011 from U.S. Appl. No. 11/233,317,Gal, Improved Sensors for Inductive Plethysmographic Monitoring Applications and Apparel Using Same, Sep. 21, 2005.
Office Action dated Jan. 27, 2011 from U.S. Appl. No. 10/991,877, Keenan, Method and system for processing data from ambulatory physiological monitoring, Nov. 18, 2004.
Office Action dated Feb. 2, 2011 from U.S. Appl. No. 11/373,822, Sackner, Systems and methods for ambulatory monitoring of physiological signs, Mar. 9, 2006.
Office Action dated Feb. 17, 2011 from U.S. Appl. No. 11/682,601, Derchak, Monitoring and quantification of smoking behaviors, Mar. 6, 2007.
U.S. Appl. No. 11/357,772, Sackner, System and Methods for Ambulatory Monitoring of Physiological Signs, filed Feb. 17, 2006.
U.S. Appl. No. 11/373,822, Sackner, System and Methods for Ambulatory Monitoring of Physiological Signs, filed Mar. 9, 2006.
U.S. Appl. No. 12/869,576, Stone, Method and System for Limiting Interference in Magnetometer Fields, filed Aug. 26, 2010.
U.S. Appl. No. 12/869,578, Derchak, Noninvasive Method and System for Monitoring Physiological Characteristics, filed Aug. 26, 2010.
U.S. Appl. No. 12/869,582, Derchak, Noninvasive Method and System for Monitoring Physiological Characteristics and Athletic Performance, filed Aug. 26, 2010.
U.S. Appl. No. 12/869,585, Derchak, Noninvasive Method and System for Monitoring Physiological and Athletic Performance Characteristics of a Subject, filed Aug. 26, 2010.
U.S. Appl. No. 12/869,586, Derchak, Physiological Database and System for Population Modeling and Method of Population Modeling, filed Aug. 26, 2010.
U.S. Appl. No. 12/869,592, Derchak, Multimodal Method and System for Transmitting Information About a Subject, filed Aug. 26, 2010.
U.S. Appl. No. 12/869,625, Derchak, Method and System for Interpretation and Analysis of Physiological, Performance, and Contextual Information, filed Aug. 26, 2010.
U.S. Appl. No. 12/869,627, Derchak, Physiological Monitoring Garment, filed Aug. 26, 2010.
U.S. Appl. No. 12/872,174, Derchak, Physiological Monitoring Garment, filed Aug. 31, 2010.
U.S. Appl. No. 12/971,193, Sackner, Systems and Methods for Ambulatory Monitoring of Physiological Signs, filed Dec. 17, 2010.
U.S. Appl. No. 12/976,080, Derchak, Methods and Systems for Monitoring Respiratory Data, filed Dec. 22, 2010.
International Search Report dated Mar. 24, 2008from PCT/US2007/82688.
Bloch et al., "Specific respiratory patters distinguish among human basic emotion," International Journal of Psychophysiology, 11:141-154 (1991).
Wilhelm et al., "Taking the laboratory to the skies: Ambulatory assessment of self-report, autonomic, and respiratory responses," Psychophysiology, 35:596-606 (1998).
International Search Report and Written Opinion of the International Searching Authority, application No. PCT/US2007/082688, dated May 8, 2008.
Fahrenberg et al., "Origins and Developments of Ambulatory Monitoring and Assessment", Progress in Ambulatory Assessment. Seattle, WA: Hogrefe and Huber (2001).
International Search Report PCT/US2007/82688 dated May 8, 2008.
Jens Blechert et al., "Identifying Anxiety States Using Broad Sampling and Advanced Processing of Peripheral Physiological Information", 1: Psychosom Med., vol. 69 (9), pp. 935-943. (2007).
Frank H. Wilhelm et al., "Distinguishing Emotional From Physical Activation in Ambulatory Psychophysiological Monitoring", 1: Biomed Sci Instum. vol. 42 pp. 458-463 (2007).
Douglas E. Lake et al., "Sample Entropy Analysis of Neonatal Heart Rate Variability", Am J Physiol Regul Integr Comp Physiol, , vol. 283, pp. R789-R797, (2002.).
Acharya, R.U., et al., "*Heart rate analysis in normal subjects of various age groups,*" BioMedical Engineering OnLine 3: 24, BioMed Central (2004).
Berntson, G.G., et al., "*Heart Rate Variability: Origins, methods, and interpretive caveats,*" *Psychophysiology 34*: 623-648, Cambridge University Press (1997).
Malik, M., "*Heart rate variability standards of measurement, physiological interpretation, and clinical use,*" *Eur. Heart J. 17*: 354-381, American Heart Association Inc.; European Society of Cardiology (1996).
Scholkopf, B. et al., "*Estimating the Support of a High-Dimensional Distribution,*" *Neural Computation 13*: 1443-71, Massachusetts Institute of Technology (2001).

\* cited by examiner

IDENTIFICATION OF EMOTIONAL STATES USING PHYSIOLOGICAL RESPONSES

1. CROSS-REFERENCE TO RELATED APPLICATIONS

This application claims the benefit of U.S. Provisional Application No. 60/863,216, filed on Oct. 27, 2006, the entire content of which is expressly incorporated herein by reference thereto.

2. FIELD OF THE INVENTION

The present invention relates to a system and method for real-time physiological monitoring to identify emotional states of a person. More particularly, the invention relates to identification of emotional states based on measured physiological responses of a person.

3. BACKGROUND OF THE INVENTION

Known methods of determining a person's emotional states generally require the monitored individuals to report on their own emotional states (self-reporting). For example, such information can be gathered by surveying the individual, either orally or by written questionnaire, after exposing the individual to an emotive stimulus or a series of stimuli. This method of quantification, however, is dependent on an individual's memory and perception of his own responses. The results, at best, provide an overall estimation of the person's previous emotional states, and will likely be more heavily influenced by the latter or more recent portions of the stimuli.

Other methods of determining a person's emotional states include development of an individual response/feedback pad or input configured for self-actuation by the individual. For example, the individual is typically exposed to a series of stimuli over a defined period, such as by watching a movie. During this period of exposure, the individual is instructed to touch a key on the pad to indicate a particular emotion or set of emotions that he may be feeling. While the results of this method may reflect a more correlated data set with respect to the stimulus/response effect, real-time monitoring is still not achieved. Additionally, this approach is limited in that it is dependent on individuals being aware of their own emotions, which may change frequently and subtly, and even at a subconscious level. Thus, the individual's self-reported response data likely only reflects relative extremes of emotion, and the temporal nature of the responses will only reflect the times at which these emotions reach a level where they are consciously perceived.

Thus, there remains a need for systems and methods for automatically and continuously monitoring a person to identify, in real-time, emotional states of the person without relying on self-reporting.

4. SUMMARY OF THE INVENTION

The present invention is directed to systems and methods of automatically identifying the emotional state of a person in real-time. A preferred method includes exposing a person to a stimulus, measuring the person's physiological response to the stimulus, and comparing the measured physiological response to a known physiological response patterns associated with various emotional states. The pattern of deviations of the measured physiological response from a baseline physiological response is determinative of an emotional state. Preferably, the baseline physiological responses are measured in the person when exposed to a neutral stimulus.

In the preferred embodiment, the measured physiological responses include one or more respiratory responses. Preferably, the measured respiratory responses include a measure of breath to breath variability, and more preferably includes a sample entropy. The measured respiratory responses may include, for example, a respiratory rate, a minute ventilation rate, a tidal volume, a tidal volume instability, an inspiratory flow rate, an expiratory flow rate, an inspiratory pause, and expiratory pause, a presence of cough, and presence of apnea or hypopnea, or a combination thereof.

In other embodiments, the measured physiological responses also include a cardiac response, a posture/activity response, a temperature response, a galvanic skin response, an EEG response, an EOG response, an EMG response, and a vocal response, or a combination thereof. Preferably, the cardiac responses include an ECG response, an RSA response, a heart rate response, and a heart rate variability response, or a combination thereof.

The identified emotional states include, for example, neutrality or indifference, fear, anxiety, excitement, happiness, sadness, attentiveness, anticipation, boredom, anger, pleasure, or calmness. The emotional state may also include a measure of the degree to which the person is engaged with, concentrated on, or focused on the stimulus.

Preferably, the baseline physiological responses are measured in the person when exposed to a stimulus known as likely to elicit a selected emotional state, and where the emotional state of the person is subsequently identified as likely to be the selected emotional state when the measured physiological responses significantly similar to the baseline physiological responses. More preferably, two sets of responses are significantly similar when the likelihood that the similarity is due to chance is less than a selected threshold.

Preferably, the method for identifying an emotional state of a person is computer-implemented. For example, one embodiment of the present invention is a monitoring system for automatically identifying an emotional state of a person in real-time. The system includes a processor, a computer readable memory operatively coupled to the processor and configured with instructions for causing the processor to perform a method for identifying emotional states, and a physiological monitoring device operatively coupled to the processor for measuring the person's physiological response. Preferably, the device is configured and arranged for monitoring an ambulatory subject. More preferably, the processor correlates the time of exposure to the stimulus and the type of stimulus with the measured physiological response.

In another preferred embodiment of the present invention, the method for automatically identifying an emotional state of a person in real-time includes exposing a person to a stimulus, measuring the person's physiological responses to the stimulus, classifying the measured responses into one or more classes by means of a classifier trained to recognize patterns of physiological responses occurring in a plurality of emotional states, and identifying a likely emotional state in dependence on the classes into which the measured responses have been classified. Preferably, the pattern of measured physiological responses includes deviations of the measured responses from baseline physiological responses, the baseline physiological responses being characteristic of an emotional state.

In another embodiment, the classifier training further includes measuring physiological responses one or more emotional states, determining feature vectors that characterize the emotional states, and grouping the determined feature vectors into groups that characterize the emotional states, the grouping including use of a learning algorithm. The method can also include scaling the determined feature vectors, or applying dimension-reduction analysis to the determined feature vectors, or both scaling and applying dimension-reduction analysis to the determined feature vectors. Preferably, the learning algorithm includes a kernel machine algorithm. The classifier training may also include extracting the determined feature vectors from the measured physiological responses, the determined feature vectors being those determined during classifier training, and applying the trained classifier to the extracted feature vectors. Preferably, scaling the extracted feature vectors, or applying dimension-reduction analysis to the extracted feature vectors, or both scaling and applying dimension-reduction analysis to the extracted feature vectors is also performed.

One of the advantages of this invention is that it eliminates potentially confounding factors associated with self-reporting (i.e., surveys, a response "box", and so forth). These confounding factors include temporal dislocation of emotional state and the act or reporting, emotional-state distortion by the intervening conscious act of self-reporting, faulty memory, suggestion, and so forth. Instead the present invention provides systems and methods of continuously and automatically monitoring physiological responses of a person to determine real-time emotional states thereof. The monitored person need not perform any conscious personal acts so that both conscious and sub-conscious emotional states can be captured.

This invention is useful in such applications as audience monitoring of various sorts. For example, it can be used to monitor audience responses to movies, plays, performances, and the like. Also it can be used to monitor responses to television programs, advertisements, radio presentations, and any other presentation of information by any media which may elicit an emotional response from individuals to which it is exposed.

This invention can also be applied to product displays and evaluations. It can be useful to monitor emotional responses to product packaging, product display, product appearance, during use of novel or established products, and so forth.

5. BRIEF DESCRIPTION OF THE DRAWINGS

The present invention may be understood more fully by reference to the following detailed description of preferred embodiments of the present invention, illustrative examples of specific embodiments of the invention, and the appended figures in which.

6. DETAILED DESCRIPTION OF THE PREFERRED EMBODIMENTS

The present invention is directed to a system and method of identifying an emotional state that a person is experiencing, preferably in real-time. Preferred monitoring systems for identifying emotional states are described, as well as preferred methods of using such systems therefore.

6.1 PREFERRED MONITORING SYSTEMS

Preferably, the physiological monitoring systems are ambulatory systems configured so that a person is not appreciably constrained. The ambulatory monitoring systems are also preferably configured for use without assistance by trained personnel. The monitoring systems include sensors, as generally known to one of ordinary skill in the art, that can be constructed according to the many known technologies useful for non-invasive physiological sensing. Preferably, selected sensors have sufficient accuracy and precision, both in amplitude and response time (i.e. bandwidth), so that the gathered signals actually reflect the physiological systems and processes of interest. The sensors preferably have clinically confirmed accuracies and precisions. A preferred ambulatory physiological monitoring system configuration includes a wearable item, for example, a garment, band, patch, and the like, or associations with partial-shirts or shirts, on partial body suits, or in full body suits that are unobtrusive, comfortable, and preferably made of non-restricting fabric into which sensors are incorporated.

Figure 1:
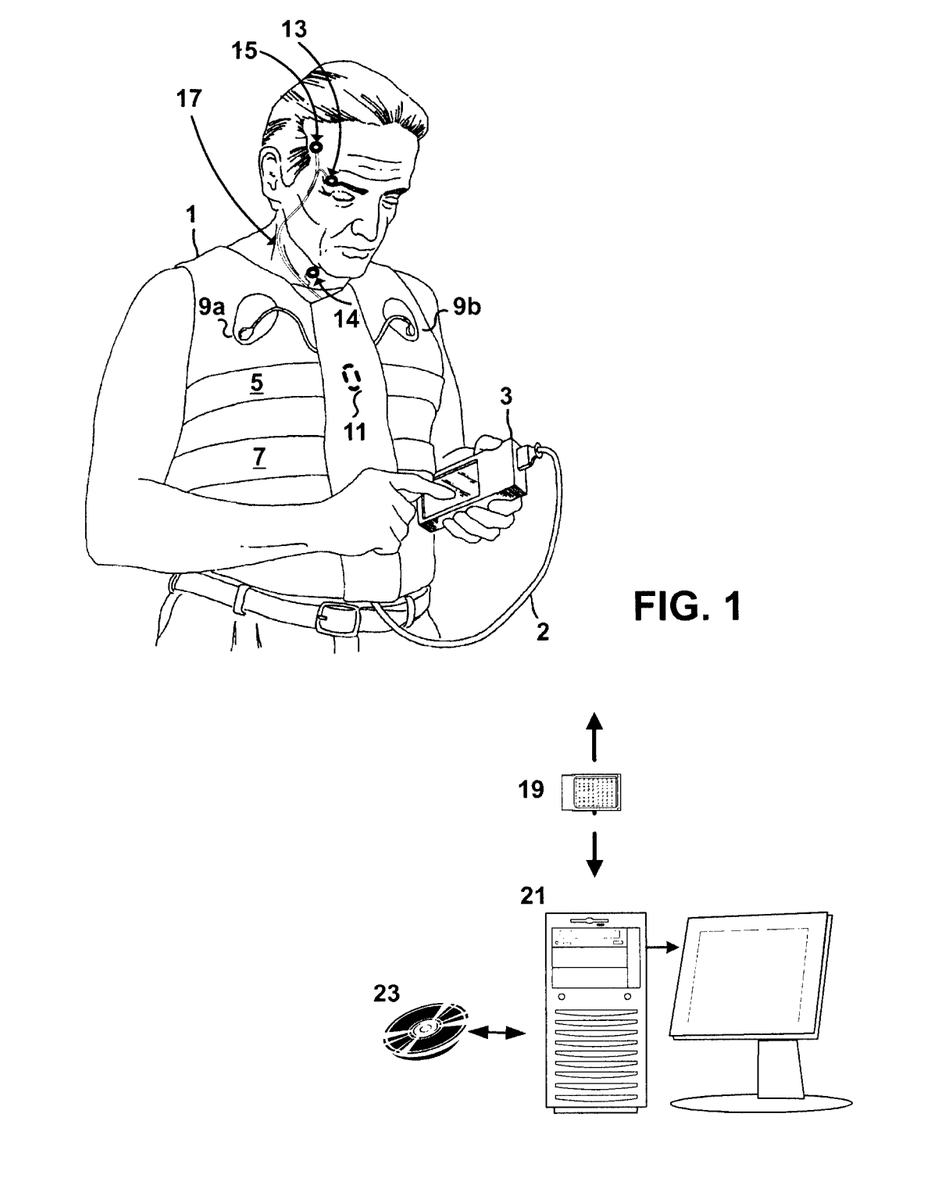
FIG. 1 illustrates depicts an embodiment of an ambulatory multiple parameter monitoring system according to the present invention.

An exemplary ambulatory monitoring system is illustrated in FIG. 1, which depicts garment or shirt 1, which is preferably sufficiently comfortable and unobtrusive so that a person is not constrained and can perform their normal daily waking and sleeping activities. Garment 1 carries, or has embedded or integrally included therein, sensors for gathering necessary monitoring data, and permits physiological recording, preferably for up to at least about an 8-hour duration.

In a preferred embodiment, an exemplary garment 1 is a LIFESHIRT® ambulatory monitoring garment available from VivoMetrics, Inc. (Ventura, Calif.). In other embodiments, the data processed by this invention can be gathered by other sensor technologies known in the art, and by other dispositions and arrangements of such sensors on the monitored person. However, for conciseness and without limitation, the following description is largely in terms of this preferred embodiment of the monitoring garment and associated system components.

The garment 1 preferably includes size sensors, and more preferably, the sensors include inductive plethysmographic (IP) sensor bands 5 and 7 (or other sensor types providing respiratory rate and volume information), one or more accelerometers and the like for sensing body posture and motion, for example exemplary accelerometer 11, and one or more microphones for detecting vocal and body sound, such as throat microphone 14. "Size sensors" gather signals responsive to size indicia describing portions of a monitored person's body, e.g., the torso, the neck, the extremities, or parts thereof. Size indicia can include the length along a selected portion of the body surface; the circumference or diameter of a body part; and the like. Garment 1 is preferably made of a stretchable material that fits in a manner so as to expand and contract with a person's body so that embedded IP sensor bands (which, for respiratory measurement, are known as respiratory inductive plethysmographic, or RIP, bands) can respond to the varying sizes of a monitored person, e.g., varying circumferences/girths or lengths of the person's torso and abdomen. One RIP band is adequate, but preferably two RIP bands are used: band 5 at the level of the rib cage, and band 7 at the level of the abdomen.

Size sensor signals can be processed to yield information about organ system functioning. Signals from size sensors at one or more levels of the torso, e.g., at an abdominal level and at a rib cage level, can be interpreted using a two-component breathing model in order to determine respiratory rates, respiratory volumes, respiratory events, and the like. U.S. Pat. Nos. 6,551,252; 5,159,935; and 4,777,962, and U.S. patent application Ser. No. 10/822,260, which are incorporated herein in their entireties for all purposes by reference thereto, describe such signal processing.

Also, the garment 1 can include sensors for monitoring cardiac information, such as heart rate, ECG, or thoracocardiaogram. See, e.g., U.S. Pat. Nos. 5,178,151 and 6,783,498. Other sensors can include thermistors that can sense skin or body core temperature; pulse oximeters that can sense blood oxygen level; capnographs; EEG electrodes (illustrated as 9a and 9b); ultrasound transducers for blood flow or organ pulsations, and so forth. EMG and EOG signals can be obtained from EMG and EOG sensors that are also preferably included in the garment 1, such as single bipolar (parietally-located) EMG sensor 15 and single-lead EOG sensor 13. The EMG and EOG sensors are preferably in electrical communication with garment 1, for example by means of electrode 17. These electrodes are preferably made of fabric, or are otherwise flexible, and provide sufficient electrical contact without the need for conductivity enhancements, such as pastes, fluids, and the like. In the hospital, clinic, or laboratory settings, other signals may be obtained from a wide range of physiological sensors.

Associated locally with exemplary garment 1 is local data recording unit 3 operatively connected to sensors of the garment 1 by data cable 2. In other embodiments, the recording unit may be operatively connected to the sensors by, for example, short range radio link. Data recording unit 3 is preferably compact and lightweight so that it can be worn on a belt, put in a pocket, or embedded in garment 1. This unit stores sensor data with sufficient accuracy and precision for such purposes as off-line analysis and medical disclosure audits, and may include a touch screen or other user input facility for implementing a digital diary whose data may also be transferred to the analysis computer for correlation with sensor readings.

Initial sensor signal processing generally includes filtering, digitization, noise limiting, extraction of physiological signal components, and the like. Following initial processing, specific processing according to the methods of this invention of respiratory size sensor signals, other sensor signals, and microphone sound data signals, for example, are preferably performed to identify emotional states according to the methods of this invention. For example, processing respiratory signals includes calibration, determination of a tidal volume signal, and extraction of respiratory events from the tidal volume signal. U.S. Pat. Nos. 6,413,225; 5,159,935; 4,834,766; and 4,777,962, and U.S. patent application Ser. No. 10/822,260, all of which are incorporated herein in their entirety for all purposes by reference thereto, describe such respiratory processing.

Signals from additional sensors are processed as appropriate. For example, R-waves can be recognized in ECG signals using known methods, and then cardiac rates and rate variability can be extracted. Electroencephalogram and similar signals can be stored for later manual grading and analysis. Accelerometer signals can be low and high pass filtered to extract posture information and activity level information, respectively. U.S. patent application Ser. No. 10/991,877 describes such signal processing.

In one embodiment, basic signal processing, e.g. filtering and digitization, is performed in the data recording unit 3. In preferred embodiments, the data recording unit also extracts physiological information and performs the methods of this invention. The methods of the present invention can be implemented by analysis software that is executed on analysis computers, such as computer 21, which may be remotely located from the subject or even at an observation locale. Analysis can be done either concurrently with signal recording (online) or at a later time (offline). For offline analysis, sensor data can be transferred from data recording unit 3 to analysis computer 21 on memory card 19, such as a compact flash card. Data may alternatively be transferred by wireless links, such as transmission using cell phone technologies and the like.

Specifically, the methods of the present invention are preferably performed on software or firmware programmable systems. In the case of software programming, methods are preferably coded in standard computer languages, such as C, C++, or in high level application languages, such as Matlab and associated toolboxes (Math Works, Natick, Mass.). Code is then translated or compiled into executable computer instructions for controlling a microprocessor or similar device. In the case of firmware programming, higher level method specifications written in software languages or hardware languages such as VHDL, are preferably translated into bit codes by tools supplied by the manufacturer of the hardware part that is being programmed. For example, manufacturer's tools can be used to prepare bit-streams for configuring FPGAs.

All or part of this analysis software implementing this invention's methods may be made available as a program product on a computer readable medium, such as optical disk 23.

6.2 PREFERRED EMOTIONAL STATE IDENTIFICATION METHODS

The present invention preferably includes methods of determining the emotional state that a person is experiencing by comparing real-time measured physiological responses to given stimuli with baseline physiological responses that were previously measured after exposure to the same or other neutral stimuli. The physiological responses are preferably measured by embodiments of the physiological monitoring systems and methods previously described. Specific emotional states include, for example, neutrality or indifference, fear, anxiety, excitement, happiness-laughter, sadness-crying, anticipation, boredom, anger-aggression, pleasure, love, tenderness, or calmness. Additionally, the method of the present invention can be used to determine a person's attentiveness or attentive state as an emotional state, i.e., the degree to which a person is engaged with, concentrated on, or focused on a particular stimulus, and thus more susceptible to experiencing an emotional state in response to that stimulus.

A preferred method of determining an emotional state includes exposing a person to a stimulus, measuring the person's physiological response to the stimulus, and comparing the measured physiological response to a known baseline physiological response. A deviation between the measured physiological response and the baseline physiological response can be determined, and if the deviation is within acceptable ranges of deviation from the baseline physiological response, the person is identified as experiencing a particular emotional state that is associated therewith.

Figure 2:
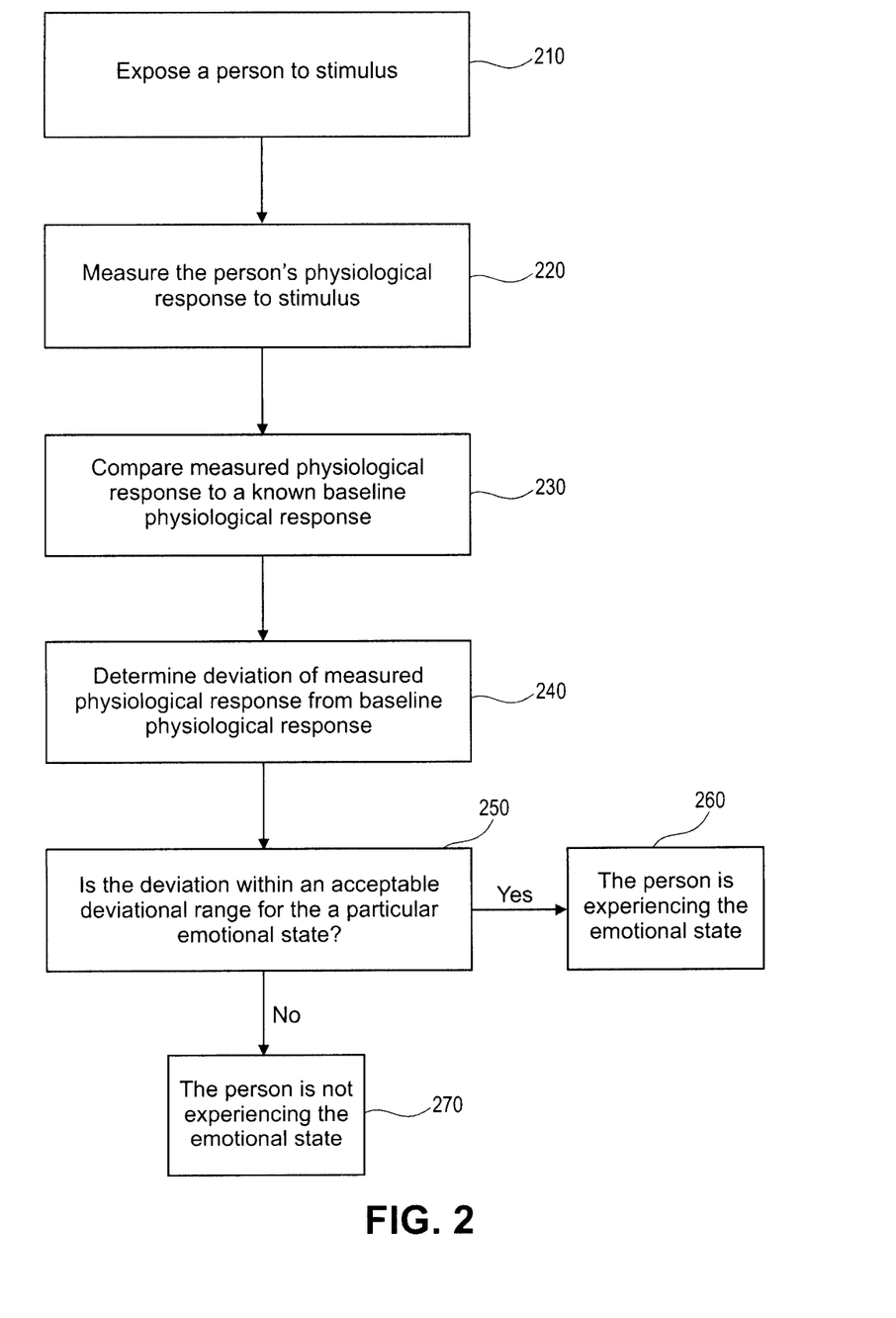
FIG. 2 illustrates one embodiment of a method for identifying emotional states.

Referring to the flowchart of a preferred method of the present invention shown in FIG. 2, initial step 210 includes exposing a monitored person to a stimulus or a series of stimuli. Such stimuli can be visual (e.g., a still image, motion picture, etc.); audio (e.g., speech, music, noise, etc.); olfactory; taste-based; and touch-based (e.g., temperature, pressure, tactile, etc.), or a combination thereof. Preferably, the person is wearing an ambulatory monitoring system (e.g., the LIFESHIRT® ambulatory monitoring garment) that allows for the continuous monitoring and observation of physiological changes associated with emotional responses. Continuous physiological monitoring can enable identification and quantification of emotional responses to stimuli that occur both consciously and also subconsciously.

While the person is being exposed to the stimuli, the person's physiological responses are monitored in real-time, as shown in step 220. Changes in emotional state can manifest in characteristic changes in many, if not most, organ systems. Responses of different organ system can be measured either in sequence or in parallel. For example, emotion-induced changes can occur in the respiratory system, the cardiac system, the integument (skin), the musculoskeletal system, and so forth. Further, emotion-induced changes can manifest in different ways in a single organ system. For example, the average values of a level, or a rate, or similar, of a physiological parameter or value can change from a baseline value to a perturbed value. Examples of such changes in physiological parameters are changes in heart rate, ECG characteristics (such as ST segment level), galvanic skin response, peripheral temperature, respiratory rate, minute ventilation, tidal volume, inspiratory or expiratory flow rates, inspiratory or expiratory times, % thoracic tidal volume, respiratory duty cycle, $CO_2$ partial pressures, unconscious motions (e.g., eye blinks, body and posture restlessness, and so forth), unconscious vocalizations, and the like. These and other physiological measures are known in the prior art. See, e.g., Wilhelm et al., 1998, *Psychophysiology* 35:596.

Also, emotions can induce changes in aspects of the temporal patterns of repetitive physiological events (other than simple changes average rates or frequencies). For example, patterns can become less regular with short term accelerations and decelerations lasting for only one to a few events; or the form of each event may be unchanged while the interval between events varies; or events of unusually large or small amplitude may be interspersed with otherwise normal events, and so forth. In particular, altered respiratory patterns can be manifested in tidal volume instability, inspiratory or expiratory flow rate or timing instabilities, inspiratory or expiratory pauses, sigh pattern and/or sigh volume, occurrences of coughs or apneas or hypopneas, and the like. Such respiratory variability appears or increases during many types of anxiety (e.g., fear). Similar instabilities can be induced cardiac measures such as heart rate, stroke volume (measured by pulse amplitude), ECG timings and amplitudes, and the like. Also, interactions of two organ systems can change, e.g., the patterns of respiratory sinus arrhythmia (periodic changes in heat rate during each breath) can be perturbed. Further variability can be manifested in body, core, or skin temperatures; galvanic or other skin-related responses; EEG, EOG, or EMG; and vocal responses, or a combination thereof.

The measured physiological responses may be monitored, collected, and/or otherwise analyzed under a number of analytical methods. For example, the data may be analyzed as raw absolute numbers, or they may be computed using root-mean-square (RMS), standard deviation (SD), and/or complex demodulation (CDM) methods. Changes in the values and rates (such as those discussed first above) can generally be adequately characterized by mean values and statistical measures of expected variation of the mean values (e.g., standard deviations (SD)). Using statistical techniques, the significance of a particular measured value can be determined by comparing it to its expected (or baseline) mean value and statistically characterizing any differences, e.g., in terms of SDs or in terms of the likelihood that the observed deviation is due to chance.

Changes in patterns and instabilities of patterns (such as those discussed second above) can be characterized by additional analysis tools which are most easily explained by example. Consider a baseline series of values (e.g. tidal volumes)—{420, 425, 425, 430}—with a mean of 425 and a SD of about 2; and also consider a measured series of values—{400, 450, 440, 470}—with a mean of 440 and a SD of about 12. Comparing the measured mean of 440 with the baseline mean of 425 and SD of 2, one concludes that the measured rate is different from the baseline rate in a statistically significant manner. But further comparing the measured SD of 12 with the baseline SD of 2, one can also conclude that the variability (regularity) of the measured series is significantly higher (lower) than the baseline series. Sample statistics of standard deviations are known, and in further embodiments, can be used to assess the statistical significance of a difference in SD values. This increase in (e.g., tidal volume) instability can also be analyzed by comparing the baseline series of differences in successive values—{5, 0, 5}—with the measured series of difference in successive values—{50, −10, +30}. SD (and also means) of the difference series can also be used to assess variability and irregularity. In further embodiment, other statistics that can be employed to assess variability include third and fourth order moments of the value or difference series, root mean squares of the difference series, and the like. For example, the RMS value of the measured difference series is about 34, which is considerably greater than the RMS value of baseline difference series of about 4.

Alternatively, signal regularity or predictability can be analyzed by entropy methods, in particular by sample entropy methods, where lower (higher) entropies indicate increased (decreased) predictability or regularity. See, e.g., Richman et al., 2000, Physiological time-series analysis using approximate entropy and sample entropy, *Am. J. Physiol. Heart Circ. Physiol.* 278: H2039-H2049. Briefly, sample entropy reflects the probability of prior signal patterns reoccurring in the future; the higher the probability, or the lower sample entropy, the more predictable and regular the signal. Sample entropy can be measured as the negative natural logarithm of an estimate of the conditional probability that two or more sub-series (epochs) of length m, which are selected from the input data series beginning at different data points of the input data series and which match within a tolerance r, also match at the next (m+1'st) data point. Other methods of analyzing signal regularity or predictability can be used in other embodiments.

Next, after determining values, measures of instabilities, and optionally their significances, it is preferred to combine some of all of this determined data into a set of physiological data that provides a "physiological fingerprint" of the measurements of the current emotional state of the monitored person. The significance of such fingerprints, also known as feature vectors, can then analyzed as described in the following. Fingerprints measured during examination situations can be compared to significant fingerprints or feature vectors to determine a likely current emotional state of the subject.

Once the individual physiological responses or combined physiological fingerprint are recorded, they are compared to known baseline physiological responses or fingerprints observed when the person was in selected emotional states, as shown in step 230. Preferably, the known baseline physiological responses and their variances are previously recorded, and stored in an electronic database in association with the particular emotion states and the particular setting (e.g., at home, in a theatre, and the like) occurring when they were monitored. The baseline is preferably stored as a limited range of discrete indices or physiological fingerprints.

For example, the method can include measuring a person's baseline respiratory rate in a particular emotional state, and storing such respiratory rate as a known baseline physiological response that includes a range of respiratory rates, i.e., having upper and lower bounds that differ by a percentage of the measured respiratory rate. Preferably, the allowable range is determined based on a normal deviation that can be expected in a healthy population for a particular physiological parameter; more preferably, the allowable range is less than a normal deviation. By storing the known baseline physiological response or fingerprint as a limited range, comparison during later steps of FIG. 2 does not have to result in an exact match in order for an emotional state to be identified. Rather, a correct match for an emotional state can be determined if the measured physiological response or fingerprint of a person falls within an acceptable tolerance range of the known baseline physiological response or fingerprint, where the tolerance is preferably based on a combinations of the variables making up the fingerprint.

In the preferred embodiment, one baseline physiological response is measured as a response to an emotional state evoked by a neutral stimulus, preferably over an extended period of time to invoke a stable and preferably resting physiological response by the person. For example, exposing the person to a neutral stimulus can include displaying a pleasant image or video, broadcasting soothing music, and instructing the person to sit or lay still, or a combination thereof. During such exposure, the person's physiological information is monitored, recorded, and stored as the baseline physiological response or fingerprint.

In an alternative embodiment, the known baseline physiological responses in particular emotional states are measured as responses to the same stimulus or series of stimuli that the person is exposed to in step 210. Similar to exposure to a neutral stimulus, the person's physiological information is monitored, recorded, and stored as the baseline physiological response or fingerprint. Using the same stimulus for obtaining the known baseline physiological response or fingerprint as is used in step 210 advantageously facilitates easier determination of an emotional state of the person because the measured and baseline responses can be directly compared to each other. Additionally, the baseline responses or fingerprints obtained in this manner can be correlated to specific emotional states (e.g., by retrospective questionnaire or interview) prior to comparison with the measured responses.

Whichever type of stimulus is used to obtain the known baseline physiological response or fingerprint, the monitored baseline data is preferably measured individually for each person. Preferably, it is previously measured at a time when the person exhibited a stable physiological condition and health to reflect the person's normal physiological parameters. Additionally, the baseline physiological response or fingerprint is preferably recently updated, e.g., preferably measured within the last two years and more preferably measured within the six months, to minimize expected physiological response deviations due to aging.

Alternatively, the known baseline physiological response can be based on a distribution of physiological responses previously measured from a group of a population of similar people. Preferably, it is selected from empirical data based on histograms or other distributions of known physiological responses or fingerprints that were collected during exposure to a stimulus or a series of stimuli. Such data is preferably representative of a large population of persons and can be stratified by different individual characteristics, such as age, height, weight, and gender.

After comparing the measured physiological response or fingerprint to the known baseline physiological response, a deviation between the two data sets can be determined, as shown in step 240. As described above, the known baseline physiological responses or fingerprints are preferably correlated with particular emotional states. In the case where a neutral stimulus is used to obtain a known baseline physiological response, particular emotional states are preferably correlated with changes in the physiological responses or fingerprints from the baseline.

Based on whether the determined deviation falls within an acceptable error or deviation range, as shown in step 250, the method identifies that the person is experiencing the particular emotion state. For a simple example, if the person's ventilation rate was measured as a physiological response to a stimulus exposure, and the measured ventilation rate falls within the acceptable range for baseline ventilation rates that correspond to the emotion of fear, then the method would identify the person is experiencing fear while the person's ventilation rate remained within that pre-determined, acceptable error range, as shown in step 260. If, however, the person's ventilation rate falls outside the acceptable error range of the baseline physiological response, then the method would identify the person as not experiencing the emotion of fear, as in step 270 (but perhaps another identifiable emotional state).

6.3 PREFERRED PARAMETER RECOGNITION METHODS

The signatures of baseline emotional states are recognized by a pattern of related changes in a number of monitored physiological parameters (rarely, only one parameter). There a number of methods known for finding and characterizing such patterns. For example, descriptions of pattern recognition methods and machine learning tools as known in the art can be found in, e.g., Duda, R. et al., *Pattern Classification*, Wiley, New York, N.Y. (2001), Vapnik, V., *Statistical Learning Theory*, Wiley, New York, N.Y. (1998), and Hastie, T. et al., *The Elements of Statistical Learning*, Springer (2001).

Figure 3:
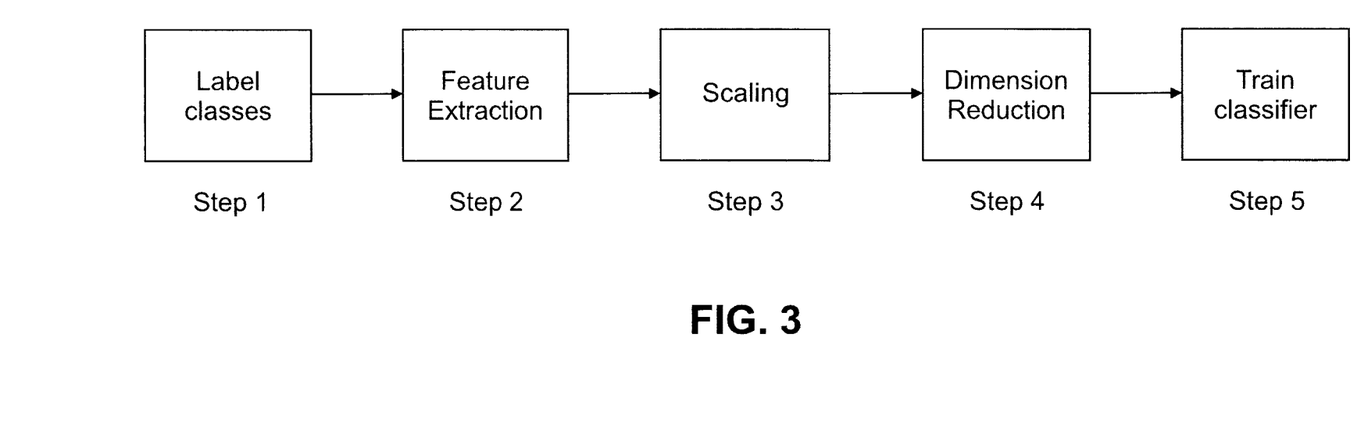
FIG. 3 illustrates a flow chart for one embodiment of a training algorithm.

Pattern recognition may be broadly defined as developing an algorithm that is able to classify an individual as experiencing one of n labeled classes (e.g., emotional states) in view of monitored physiological responses and parameters. One approach uses a-priori data (already observed stimulus-response data) to train a selected algorithm. Presentation of observed data along with the experienced emotional states to a classification training algorithm teaches the classifier (i.e., generates parameters that define a specific classifier) to recognize the distinctions between each of the classes that are present. In one example, the classifier trainer creates a set of decision boundaries so that when a new data (multidimensional) point is presented to the classifier, the classifier may determine in which boundary it resides and then label it accordingly. FIG. 3 is a flow chart that shows steps 1-5 of one embodiment for training a classification system for use in pattern recognition.

Step 1 preferably includes labeling the relevant classes (e.g., emotional states). For example, this can be simply assigning an integer label for each of the n classes, e.g., $c_j=1, \ldots, n$. Step 2 preferably includes extracting relevant features (e.g., parameter boundaries in an n-dimensional space) from the data that will be used to uniquely identify each class. In certain embodiments, sets of features can be manually selected and the remaining steps of FIG. 3 are performed to determine if the manually-selected features lead to adequate performance of the trained classifier. If the performance is not satisfactory, a different set of features can be manually selected and the process of FIG. 3 is repeated until adequate performance is achieved. Preferred embodiments include automatically selecting features; performing the steps of FIG. 3 to determine whether the classifier performance is satisfactory. If satisfactory performance is not achieved, another set of features can be automatically selected and the illustrated steps can be repeated Once adequate performance is achieved, the selected features are can be put together to form a feature vector. The dimension D of this vector (which is the same as the dimension of the feature space) is preferably the number of features used, and each component in the feature vector is preferably a scalar component. Following feature extraction, step 3 preferably scales the data representing the features in an appropriate manner. For example, a linear transform can be performed to ensure that the data lie in the range [0,1] or [−1,1].

The dimension reduction of step 4 preferably includes, in one embodiment, a principal components analysis. This analysis transforms correlated feature variables (if any) into a preferably smaller number of uncorrelated feature variables called principal components. After this analysis, the first principal component accounts for as much of the variability in the data as possible, and each succeeding component then accounts for as much of the remaining variability as possible. As a result, components that account for very little variability in the feature space can be discarded.

The final step 5 includes selection of an appropriate learning algorithm to train the classifier. Preferably, the scaled and reduced feature vectors used for training are presented to the learning algorithm, i.e., for each class, a representative set of training data is labeled as belonging to that class. The algorithm can, for example, fit multi-dimensional decision boundaries between each class. A preferred learning algorithm for emotional state identification is the support vector machine ("SVM"), see e.g. B. Scholkopf et al., Estimating the Support of High-Dimensional Distribution, *Neural Computation,* 13:7, 1443-1471 (2001) or neural network classifier. Embodiments of this invention also include automatically selecting important features by repeating the steps of FIG. 3 until the performance of the trained classifier is satisfactory. The learning scheme may be supervised (as described above) or unsupervised. Unsupervised learning or clustering may be one way to form 'natural groupings' or clusters of patterns. In other words, no a-priori groupings or classes are available and the algorithms preferably seek to define an appropriate set of classes.

Figure 4:
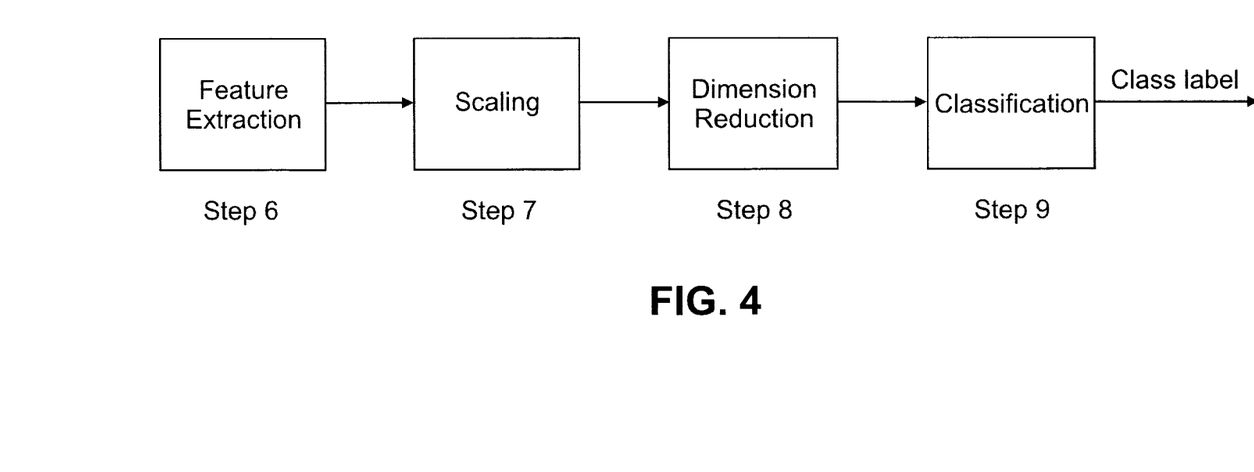
FIG. 4 illustrates a flow chart for one embodiment of a classifying algorithm.

Once a particular classifier system has been trained, new monitored physiological data can be classified, as shown in FIG. 4. Steps 6-8, although generally similar to steps 2-4, make use of information determined by the previous steps 2-4. Specifically, steps 6-8 use the determined features and also the transformation to uncorrelated variables of reduced dimensionality that have been determined during training steps 2 and 4. Where step 4 applies a principal components analysis to determine definitions of principal components of reduced dimensionality, step 8 uses these definitions to determine actual principal components that reflect the one or more of features extracted from actual monitoring data. The step 9 uses the classifier that has been trained in step 5 to classify the determined actual principal components.

Thus, the classification step method at step 6 receives input signals describing a subject and extracts the particular features of importance determined during training. Step 7 scales the extracted features in a manner similar to the scaling performed in step 3. Step 8 combines the scaled features into the important characterizations of reduced dimensionality (e.g., the determined principal components) that have been previously determined during training. Then step 9 applies the previously-trained classifier to the characterizations determined in step 8 in order to find the likely class (e.g., emotional state) for the subject described by the input physiological signals.

In the present invention, the class or emotional state of a subject being monitored is preferably determined from one the emotional states of the subject on which the classification algorithm has been trained, or one of the emotional states that the algorithm is generally trained on based on previously collected data from a distribution of subjects. If a determined emotional state matches, within an allowed deviational range, the class identified by the algorithm based on physiological data obtained from the subject under test, then that subject is confirmed as associated with such class, i.e. the subject is identified as experiencing the particular emotional state. If, however, the determined and the identified classes do not match, or if no likely matching class is found, the subject is not confirmed as associated with such class or emotional state.

ECG Parameter Recognition

A specific application of the above method can be using measured ECG signals to identify for emotional states. In a preferred embodiment, for example, changes in heart rate variability are measured for use as an indication of sympathetic nervous system activity. Extracted features can be combined to form a feature vector that is preferably used as the primary representation or indicator for comparing measured physiological parameters to baseline physiological parameters.

Figure 5:
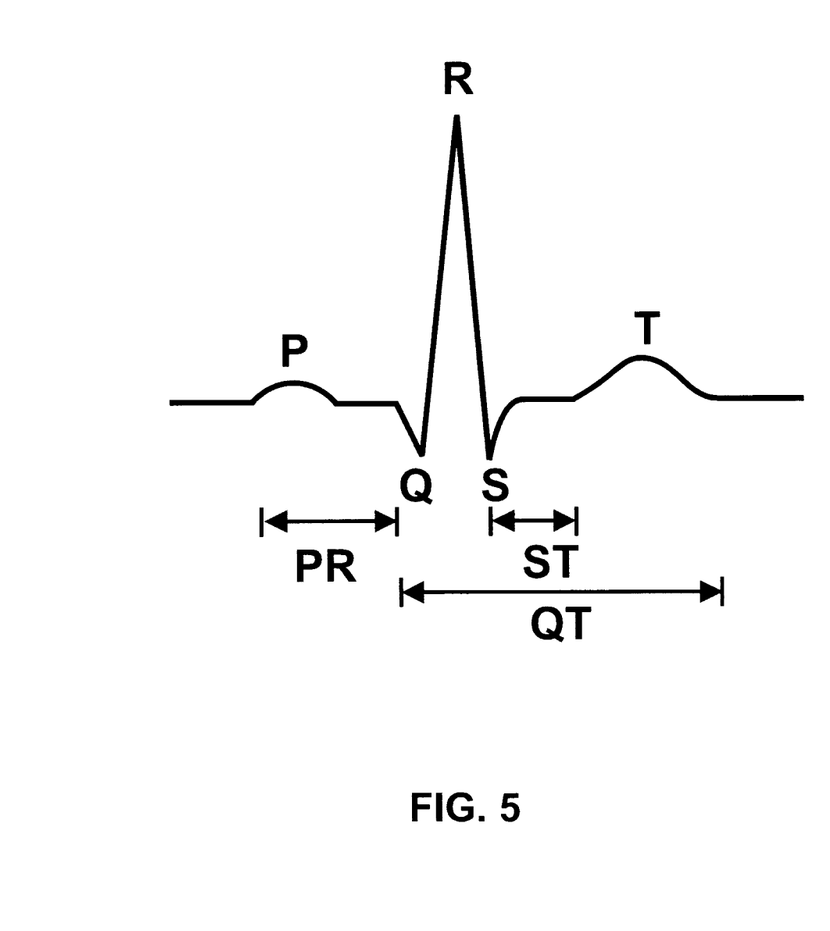
FIG. 5 illustrates an ECG representation of a single heartbeat.

Preferably, the first step in ECG feature extraction is to identify each heart beat, e.g., by identifying the QRS complex. Several standard R-wave detection and QRS detection algorithms are known, such as that disclosed by Kohler et al., *The Principles of Software QRS Detection,* IEEE Engineering in Medicine and Biology (2002), and any of these would be suitable to detect the QRS complex. In addition, the P-wave and T-waves may also be identified such that a single heartbeat can then be defined from the beginning of the P-wave to the end of the T-wave, as shown in FIG. 5.

It is well known that components of cardiac timing are under autonomic system (ANS) control. In a healthy individual, for example, it is the net effect of the parasympathetic (vagus) nerves (decelerate heart rate) and the sympathetic nerves (accelerate heart rate) that dictate the instantaneous heart rate. Furthermore, changes to mental and emotional states may induce changes to these nervous responses, thereby changing the beat to beat timing of the heart. The goal of heart rate variability (HRV) analysis is to work backwards, starting with the beat to beat variability, to obtain a picture of emotional changes. Analysis of the beat to beat variability or HRV advantageously offers a means to evaluate changes in sympathetic and parasympathetic input to the heart. In turn, changes to these inputs, when placed in environmental context, may correlate with changes to emotional state.

HRV analysis may be used to select a set of features that in turn may be used to train a statistical learning machine for emotional classification. The determination of these features is well documented in the literature (see, e.g., Heart rate variability: Standards of measurement, physiological interpretation, and clinical use, Task Force of the European Society of Cardiology and the North American Society of Pacing and Electrophysiology, Eur. Heart J., 1996 March, 17(3):354-81; Acharya et al., Heart rate analysis in normal subjects of various age groups, Biomed. Eng. Online, 2004 Jul. 20, 3(1):24; Berntson et al., Heart rate variability: Origins, methods, and interpretive caveats, Psychophysiology, 1997 November, 34(6):623-48), and features are preferably broadly classified into 1) time domain indices; 2) frequency domain indices; and 3) non-linear indices. Preferably, a feature set includes a combination of several of these calculated over an appropriate length time range of interest.

In addition to ANS input, there exists a natural cycle of heart rate variation that occurs through the influence of breathing on the flow of sympathetic and vagus (parasympathetic) impulses to the sinoatrial node. This is called respiratory sinus arrhythmia (RSA). As noted above, the rhythm of the heart is primarily under the control of the vagus nerve, which inhibits heart rate and the force of contraction. When a person inhales, the vagus nerve activity is impeded and heart rate begins to increase. Upon exhalation, this pattern is reversed, i.e., heart rate accelerates during inspiration and decelerates during expiration. This alternating pattern of acceleration and deceleration corresponds to high frequency changes in the HRV and the high frequency power is preferably used as an index of RSA and hence parasympathetic activity or vagal tone.

Individual changes within respiratory parameters of rate and tidal volume (Vt), however, can seriously confound the association of RSA and cardiac vagal tone. Decreased Vt and increased breathing frequency (Fb), or respiration rate, can profoundly attenuate RSA under conditions in which cardiac vagal tone remains constant. Thus, measuring HRV alone may be insufficient and these measurements are preferably adjusted based on the individual's breathing parameters. Adjustment for respiratory parameters has been shown to substantially improve relations between RSA and significantly vagally mediated HR and physical activity. In other words, concurrent monitoring of respiration and physical activity enhances the ability of HRV to accurately predict autonomic control. Typical adjustments preferably include determining the frequency of RSA and excluding this band from any derived frequency domain indices; normalizing indices by Vt or Fb; or by some quantification of the strength of RSA.

The particular learning algorithm used with the present invention can be selected from algorithms known in the art, for example, linear discriminate functions, probability distribution, estimation and clustering, support vector and other kernel machines, neural networks, and/or boosting algorithms. A preferred learning algorithm for identification of emotional states is an SVM, and more preferably a multi-class SVM, which enables discrimination between multiple classes. In other embodiments, for example where only a single class is targeted, the one-class SVM by Scholkopf et al. is preferred because it fits a tight bound to a single class with no information about other classes. Thus, if a new feature vector falls within this bound, it belongs to this class or is associated with this person; otherwise it is rejected as not being of this class or associated with this person.

Speech or Vocal Pattern Parameter Recognition

A further specific application of the above methods can be measuring breath and speech combinations as an identifier for emotional states is described below in more detail. This application includes material already described in patent publication WO 2006/002338A2, published Jan. 5, 2006 and titled "Systems and Methods for Monitoring Cough", which is included herein by reference in its entirety for all purposes.

Preferably, a microphone or other sound recorder creates a provided audio sample represented by associated traces. The following preferred features are then identified and extracted from a provided audio sample: 1) sound envelope, 2) event marker trace, 3) pitch, 4) sound energy, 5) duration, and 6) peak fraction.

The sound envelope ("SE") is the trace of the audio signal that is preferably captured from a throat microphone ("MIC"), and downsampled from 1500 Hz to, e.g., 50 Hz. Every, e.g., 30 data points are preferably normalized and summed to give a low resolution envelope. The event marker trace ("EVT") is a binary trace preferably at the same resolution as the SE trace. It is ON when the SE trace rises above a threshold (e.g., a relative amplitude value of 60) and goes OFF when it drops below another threshold (e.g., 30) for 3 consecutive samples.

Pitch is preferably evaluated using the Mel cepstrum of the raw MIC trace. A cepstrum is the result of taking the Fourier Transform (FT) of the decibel spectrum as if it were a signal. The cepstrum is preferably defined as the FT of the log (with unwrapped phase) of the FT, that is:

$$\text{cepstrum of signal} = FT(\log(FT(\text{the signal})) + j2\pi m),$$

where m is the integer required to properly unwrap the angle of the complex log function.

There is a real cepstrum and a complex cepstrum. The real cepstrum preferably uses the logarithm function defined for real values, while the complex cepstrum uses the complex logarithm function defined for complex values as well. The complex cepstrum holds information about magnitude and phase of the initial spectrum, allowing reconstruction of the signal. The real cepstrum only uses the information of the magnitude of the spectrum.

The cepstrum is a useful feature vector for representing the human voice and musical signals. This technique can advantageously separate the energy resulting from vocal cord vibration from the "distorted" signal formed by the rest of the vocal tract. For such applications, the spectrum is preferably first transformed using the Mel frequency bands. The result is called the Mel Frequency Cepstral Coefficients (MFCC), and can be used for voice identification, pitch detection and other analysis.

Sound energy is the integral of the SE trace over the duration of the EVT event. Duration is the length in milliseconds of the EVT ON period (i.e., sound event). Peak fraction refers to the peak of the SE trace for each event expressed as a fraction of the total EVT duration (e.g., (Peak location−Start)/(End−Start)).

The EVT trace is then preferably used to mark sections of the breath traces, where the following additional features are extracted:

ViVol, which is the inspired tidal volume of the breath that begins just preceeding the EVT marking;

Hfb, which is the raw abdominal contribution to tidal volume band bandpass-filtered between 1 and 5 Hz, where the abdominal and rib cage contributions to tidal volume can be measured with RIP sensors at the level of the abdomen and the rib cage, respectively;

Lfb, which is the rw abdominal contribution to tidal volume band bandpass-filtered between 0.1 and 1 Hz;

Maximum deflection, which is calculated for both Hfb and Lfb. The maximum peak—trough of consecutive peaks and troughs are determined for these filtered traces during each EVT;

Insp./Exp. ratio, which is the ratio of the percentage of the EVT during inspiration and that during expiration;

Center fraction, which is the location of the minimum trough as determined from the Hfb trace, is calculated as a fraction of the event time;

Turning points, which is the number of peaks and troughs as also determined from the Hfb trace over the duration of the EVT ON;

AB baseline, which is the mean value of abdominal contribution to tidal volume band for 5 seconds before and after the event; and Phase, which is the phase difference between the ribcage contribution to tidal volume band and the abdominal contribution to tidal volume band.

In other embodiments, a combination of sound and breath signatures may be used to identify both speech epochs as well as other non-speech vocalizations, such as cough, laughter, snoring, hic-cough, etc. These identifications may then be used as actual features for an emotional state classification. This results in two nested classification tasks. Speech identification would preferably include, in addition to the above features, other features such as inhalation: exhalation times ratio; the number of turning points on a single exhalation; and the number of neighboring sound events.

Following feature extraction, the data is preferably scaled. Next, it is subject to a dimension reduction process, e.g., principal components analysis, which finds a limited number of significant combinations, i.e., that account for a large part of the data variance. Based on the identified combination of all these extracted features, a reduced-dimension feature vector representative of breath and speech is created and processed to train a classifier.

Another method for identifying emotional states is based on respiratory, facial, and postural responses, as disclosed in the article by Block et al., *Specific Respiratory Patterns Distinguished Among Human Basic Emotions*, International Journal of Psychophysiology, 1, pp. 141-154 (1991).

6.4 EXAMPLES

The following examples are presented for the purposes of illustration and are not to be regarded as limiting the scope of the invention or the manner in which it can be practiced.

Example 1

Measured Physiological Responses for an Actress

Figure 6:
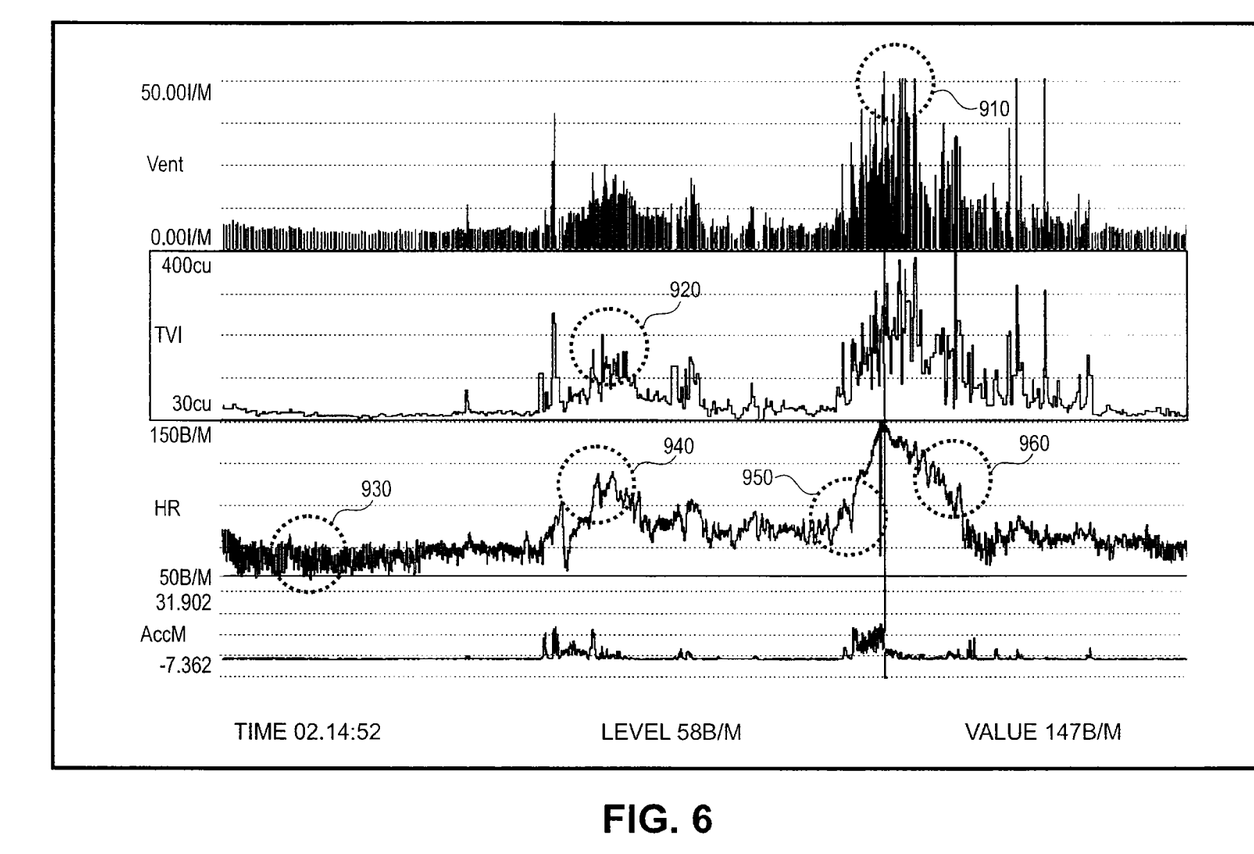
FIG. 6 illustrates exemplary measurements used for identifying emotional states of a person.

FIG. 6 shows real-time monitoring data for ventilation rate ("Vent"), tidal volume ("TVI"), heart rate ("HR"), and accelerometry ("AccM") sensors for an actress ("subject") who wore the LIFESHIRT® during a theatrical performance. During the monitoring period, the subject was initially backstage before she made her entrance on stage. The subject, however, missed her entrance queue, and the monitored data reflect her physiological responses accordingly.

For example, period 930 indicates the time when the subject was sitting backstage awaiting her entrance. Her accelerometer reading is minimal, and her heart rate was steady and stable at about 58 beats/min over this period. This data can be used as a baseline physiological response or fingerprint during exposure to a neutral stimulus when the subject is calm and at ease.

As her onstage entrance time approaches, her ventilation rate, tidal volume, and heart rate all begin to increase as she experiences increased anxiety. The sharp spike in ventilation rate corresponds to the time she was supposed to enter on stage. As can be seen in periods 920 and 930, the subject experiences increased and unstable tidal volume, and her heart rate jumps up to about 122 beats/min as she realizes that she missed her entrance. Corresponding emotions include high anxiety, stress, and fear.

Her heart rate drops slightly and stabilizes as she waits backstage before she decides to finally make her late entrance at period 950, which is associated with a sharp increase to peak heart rate of about 147 beats/min and peak ventilation of about 48 L/min, as shown in period 910. Once on stage, the subject settles into her role, which corresponds to period 960 that shows a slow recovery and stabilization of heart rate.

From the monitored data, it is evident that the subject's physiological responses to varying stimuli create discrete periods. These periods are then extracted and associated/compared with known physiological responses according to the present invention to identify emotional states that the subject is experiencing.

The term "about," as used herein, should generally be understood to refer to both the corresponding number and a range of numbers. Moreover, all numerical ranges herein should be understood to include each whole integer within the range.

While illustrative embodiments of the invention are disclosed herein, it will be appreciated that numerous modifications and other embodiments can be devised by those of ordinary skill in the art. Features of the embodiments described herein can be combined, separated, interchanged, and/or rearranged to generate other embodiments. Therefore, it will be understood that the appended claims are intended to cover all such modifications and embodiments that come within the scope of the present invention.

A number of patents, patent applications, and references are cited herein, the entire disclosures of which are incorporated herein, in their entirety, by reference for all purposes. Further, none of these references, regardless of how characterized above, is admitted as prior to the invention of the subject matter claimed herein.

What is claimed is:

1. A method for automatically identifying a likely emotional state in real-time comprising:
   exposing a person to a stimulus;
   measuring the person's physiological responses to the stimulus using a physiological monitoring device;
   comparing the measured physiological responses to baseline physiological responses using a processor, wherein:

the baseline physiological responses of the person are measured when exposed to a stimulus known as likely to elicit a selected emotional state, and the stimulus used to elicit the person's baseline physiological responses and the stimulus used to elicit the person's measured physiological responses are the same type;

recording and storing the baseline physiological responses as an acceptable range in an electronic database, wherein the baseline physiological responses are in association with particular emotional states;

the processor determining the degree to which the person is engaged with, concentrated on, or focused on the stimulus; and the processor identifying a likely emotional state in dependence on the pattern of deviations of the measured physiological responses from the acceptable range of the baseline physiological responses and in dependence on the degree to which the person is engaged with, concentrated on, or focused on the stimulus, wherein the measured physiological responses and baseline physiological responses include both standard deviation and instability values, and wherein the measured physiological responses and baseline physiological responses comprise respiratory responses.

2. The method of claim 1, wherein the measured respiratory responses comprise a measure of breath to breath variability.

3. The method of claim 2, wherein the measure of breath to breath variability comprises a sample entropy.

4. The method of claim 1, wherein the measured respiratory responses comprise a respiratory rate, a minute ventilation rate, a tidal volume, a tidal volume instability, an inspiratory flow rate, an expiratory flow rate, an inspiratory pause, an expiratory pause, a presence of cough, or presence of apnea or hypopnea, or a combination thereof.

5. The method of claim 1, wherein the measured physiological responses further comprise a cardiac response, a posture/activity response, a temperature response, a galvanic skin response, an EEG response, an EOG response, an EMG response, or a vocal response, or a combination thereof.

6. The method of claim 5, wherein the cardiac responses comprise an ECG response, an RSA response, a heart rate response, or a heart rate variability response, or a combination thereof.

7. The method of claim 1, wherein the emotional state comprises neutrality, indifference, fear, anxiety, excitement, happiness, sadness, attentiveness, anticipation, boredom, anger, pleasure, or calmness, or a combination thereof.

8. The method of claim 1, wherein the emotional state comprises a measure of the degree to which the person is engaged with, concentrated on, or focused on the stimulus.

9. The method of claim 1, wherein identifying the likely emotional state further depends on the measured physiological responses being significantly similar to the baseline physiological responses, the baseline physiological response and the measured physiological response being defined as significantly similar when the likelihood that the similarity is due to chance is less than a selected threshold as defined through a measure of statistical significance.

10. The method of claim 1, wherein identifying a likely emotional state occurs based on conscious and subconscious responses of the person.

11. The method of claim 1, wherein the plurality of emotional states comprises fear, no fear, and excitement.

12. A monitoring system for automatically identifying an emotional state of a person in real-time, comprising:

a processor;

a physiological monitoring device operatively coupled to the processor for measuring the person's physiological response, the device being configured for monitoring an ambulatory subject; and a computer readable memory operatively coupled to the processor and configured with instructions for causing the processor to compare measured physiological responses obtained using the physiological monitoring device to baseline physiological responses, wherein:

the baseline physiological responses of the person are measured when exposed to a stimulus known as likely to elicit a selected emotional state, and the stimulus used to elicit the person's baseline physiological responses and the stimulus used to elicit the person's measured physiological responses are the same type;

the processor recording and storing the baseline physiological responses as an acceptable range in an electronic database in the computer, wherein the baseline physiological responses are associated with particular emotional states;

the processor determining the degree to which the person is engaged with, concentrated on, or focused on the stimulus; and the processor identifying a likely emotional state in dependence on the pattern of deviations of the measured physiological responses from the acceptable range of the baseline physiological responses, in dependence on the degree to which the person is engaged with, concentrated on, or focused on the stimulus, and in dependence on the measured physiological responses being significantly similar to the baseline physiological responses, the baseline physiological response and the measured physiological response being defined as significantly similar when the likelihood that the similarity is due to chance is less than a selected threshold as defined through a measure of statistical significance of both standard deviation and instability, wherein the measured physiological responses and baseline physiological responses comprise respiratory responses.

13. The monitoring system of claim 12, wherein the processor correlates a time of exposure to the stimulus and the type of stimulus with the measured physiological response.

14. A method for automatically identifying an emotional state of a person in real-time, comprising:

exposing a person to a stimulus;

measuring the person's physiological responses to the stimulus with a physiological monitoring device configured to measure physiological responses comprising a respiratory and a cardiac response;

classifying the measured physiological responses into classes with a processor including a classifier trained to recognize patterns of physiological responses based on discrete periods of physiological data collected from a distribution of a population of people, and occurring in a plurality of emotional states, wherein training the classifier comprises measuring physiological responses, identifying discrete periods of physiological responses to the stimulus, selecting features to be used to identify each class, and grouping the selected features into groups that characterize the emotional states; and identifying a likely emotional state with the processor in dependence on the classes into which the measured responses have been classified if the measured response matches one of the plurality of emotional states or falls within a predetermined deviational range of one of the plurality of emotional states according to both standard deviation and instability, wherein the emotional state comprises a measure of the degree to which the person is engaged with, concentrated on, or focused on the stimulus.

15. The method of claim 14 wherein a pattern of measured physiological responses comprises deviations of the measured responses from baseline physiological responses, the baseline physiological responses characteristic of an emotional state.

16. The method of claim 14, further comprising scaling determined feature vectors, applying dimension-reduction analysis to the determined feature vectors, or both scaling and applying dimension-reduction analysis to the determined feature vectors.

17. The method of claim 14, wherein classifying further comprises:

extracting determined feature vectors from the measured physiological responses, the determined feature vectors being those determined during classifier training; and applying the trained classifier to the extracted feature vectors.

18. The method of claim 17 further comprising scaling the extracted feature vectors, or applying dimension-reduction analysis to the extracted feature vectors, or both scaling and applying dimension-reduction analysis to the extracted feature vectors.

* * * * *